United States Patent [19]

Hickey

[11] Patent Number: 5,048,532

[45] Date of Patent: Sep. 17, 1991

[54] METHOD AND APPARATUS FOR MEASURING BLOOD PRESSURE

[75] Inventor: Donald D. Hickey, Buffalo, N.Y.

[73] Assignee: State University of New York, Albany, N.Y.

[21] Appl. No.: 409,041

[22] Filed: Sep. 18, 1989

[51] Int. Cl.$^5$ .......................... A61B 5/02; A61B 5/021
[52] U.S. Cl. ..................................... 128/675; 128/672; 128/780; 128/687; 128/673
[58] Field of Search ............... 128/668, 672, 673, 675, 128/687, 780

[56] References Cited

U.S. PATENT DOCUMENTS

| | | | |
|---|---|---|---|
| 4,214,593 | 7/1980 | Imbruce et al. | 128/748 |
| 4,502,490 | 3/1985 | Evans et al. | 128/780 |
| 4,517,984 | 5/1985 | Perlin | 128/642 |
| 4,729,384 | 8/1988 | Bazenet | 128/691 |

OTHER PUBLICATIONS

Lategola and Rahn, *A Self-Guiding Catheter for Cardiac and Pulmonary Arterial Catheterization and Occlusion*, 84 Proc. Soc. Exp. Biol. Med. 667–668 (1953).

Swan, Ganz, Forrester, Marcus, Diamond and Chonette, *Catherization of the Heart in Man With Use of a Flow–Directed Balloon–Tipped Catheter*, 283:9 The New England J. Med. 447 (1970).

J. M. Gore et al., *Handbook of Hemodynamic Monitoring*, 3 (1985).

Gore et al., *A Community–Wide Assessment of the Use of Pulmonary Artery Catheters in Patients with Acute Myocardial Infarction*, 92:4 Chest 712 (10/87).

Murray, *Complications of Invasive Monitoring*, 15:2 Medical Instrumentation 85 at p. 89 (Mar.-Apr. 1981).

Robin, *Death by Pulmonary Artery Flow–Directed Catheter* (editorial) *Time for a Moratorium?*, 92:4 Chest 727 (Oct. 1987).

Robin, *The Cult of the Swan–Ganz Catheter, Overuse and Abuse of Pulmonary Flow Catheters*, 103:3 Annals of Internal Medicine 445 (9/1985).

Rowley, Clubb, Smith and Cabin, *Right–Sided Infective Endocarditis as a Consequence of Flow–Directed Pulmonary–Artery Catheterization*, 311:18 The New England J. Med. 1152 (Nov. 1, 1984).

H. R. Anderson and P. Pless, *Trans–Esophageal Pacing*, 6 Pace 674 (Jul.-Aug. 1983).

R. P. Lasser and L. Loewe, *Characteristic Pressure Pulses Recorded with an Esophageal Balloon in Experimental Mitral Insufficiency in Dogs*, Proc. Soc. Experimental Biol. Med. 77:798 (1951).

R. P. Lasser and L. Loewe, *Esophageal Pressure Pulse Patterns (Esophageal Piezocardiogram)*, Am. Heart J. 44:531 (1952).

A. C. Taquini, *The Esophageal Pulse Under Normal and Abnormal Conditions*, Am. Heart J. 20:2 (1940).

M. Zoob, *The Esophageal Pulse in Mitral Valve Disease*, Brit. Heart J. 16:39 (1954).

A. J. Gordon, L. Kuhn, S. S. Amram, E. Donoso, E. Braunwald, *Left Atrial, "Pulmonary Capillary," and Esophageal Balloon Pressure Tracings in Mitral Valve Disease*, Brit. Heart J. 18:327–340 (1956).

*Primary Examiner*—Ruth S. Smith
*Assistant Examiner*—Robert L. Nasser, Jr.
*Attorney, Agent, or Firm*—Robert P. Simpson; Michael L. Dunn

[57] ABSTRACT

A method and appartus are provided for measuring left atrial pressure by inserting a sensing probe into the esophagus and positioning the probe so that pressure from the left atrium is sensed by the probe. More particularly, the invention provides a method for measuring left atrial pressure by inserting a balloon-containing catheter into the esophagus and positioning the catheter so that when the balloon is inflated, pressure from the left atrium affects the balloon; inflating the balloon; and, determining the left atrial pressure by the effect of the atrial pressure upon the balloon.

23 Claims, 11 Drawing Sheets

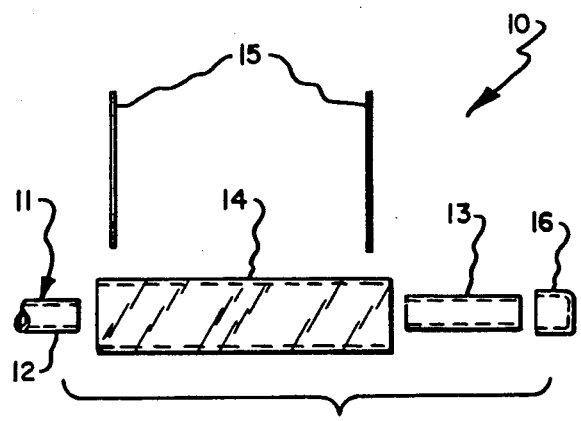
Fig. 1A.
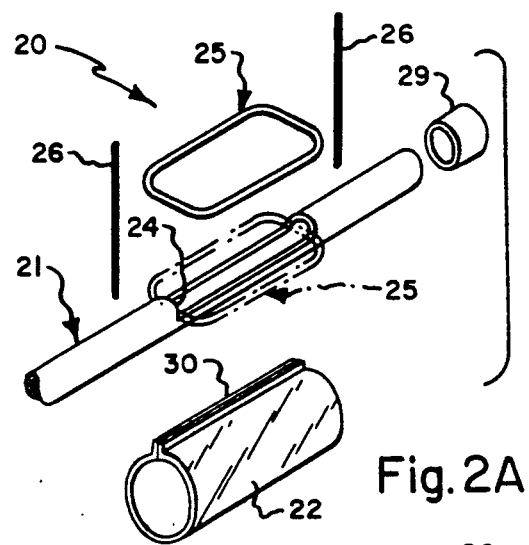
Fig. 2A.
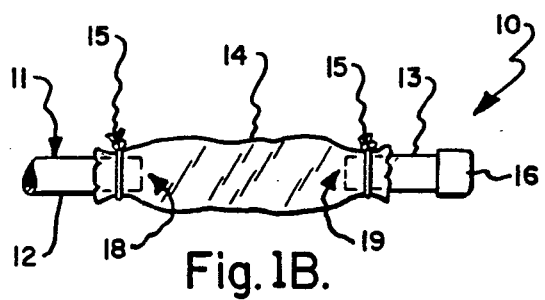
Fig. 1B.
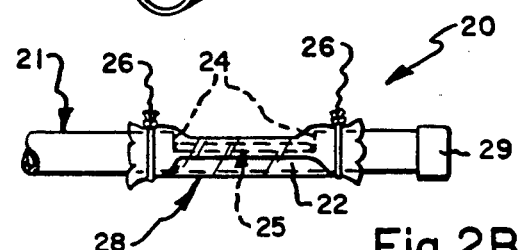
Fig. 2B.
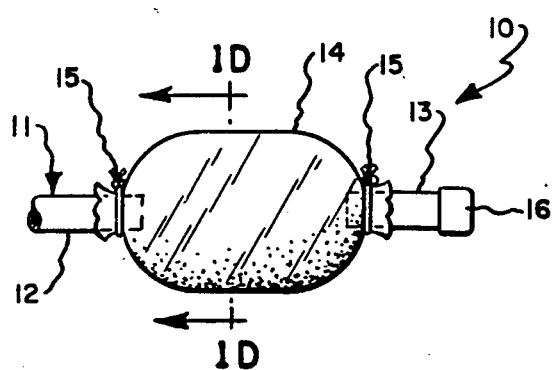
Fig. 1C.
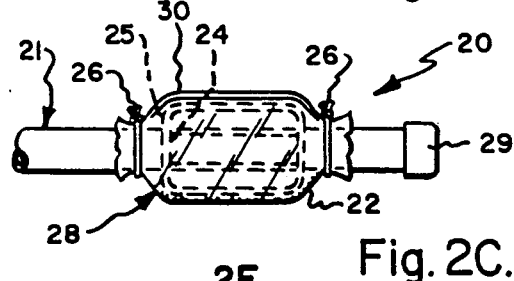
Fig. 2C.
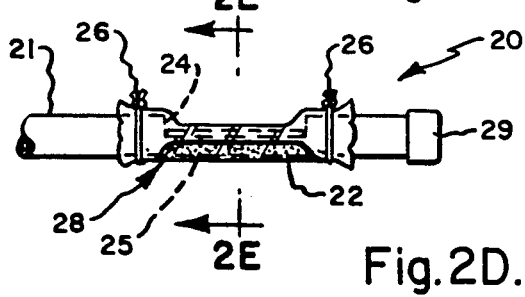
Fig. 2D.
Fig. 1D.
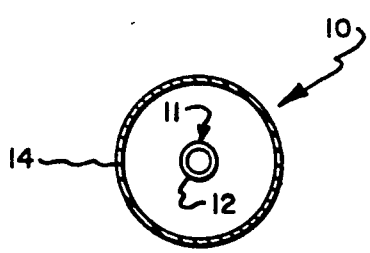
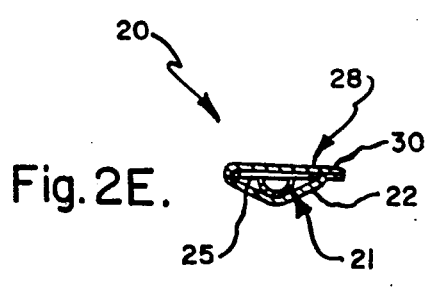
Fig. 2E.

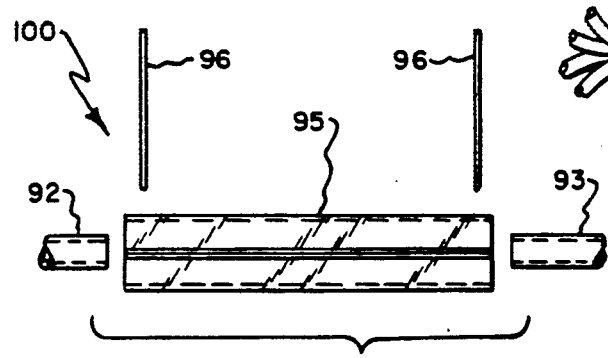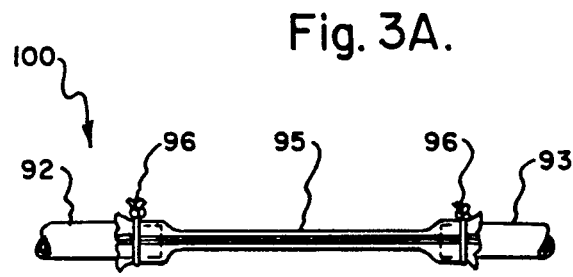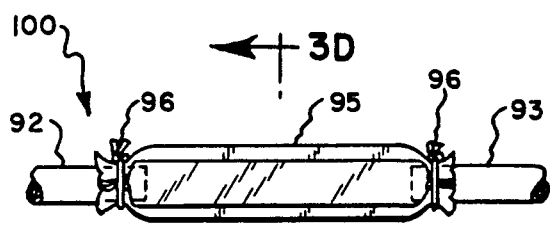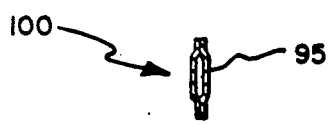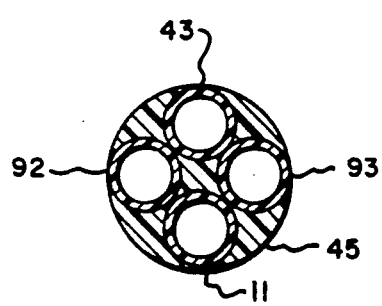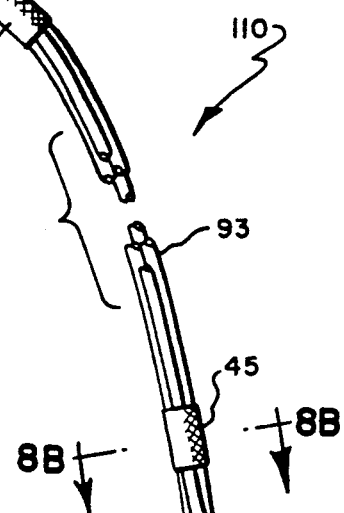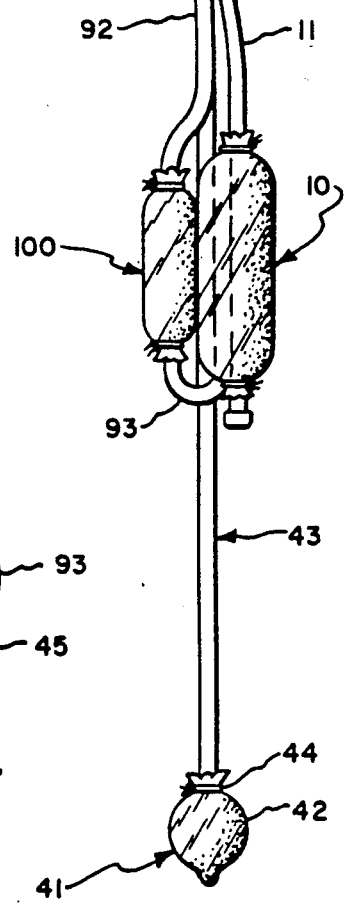

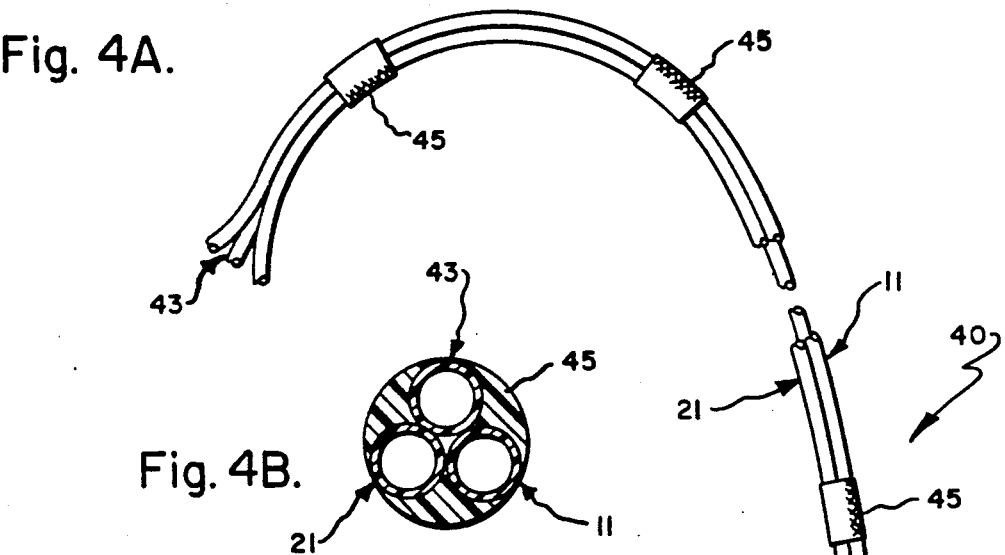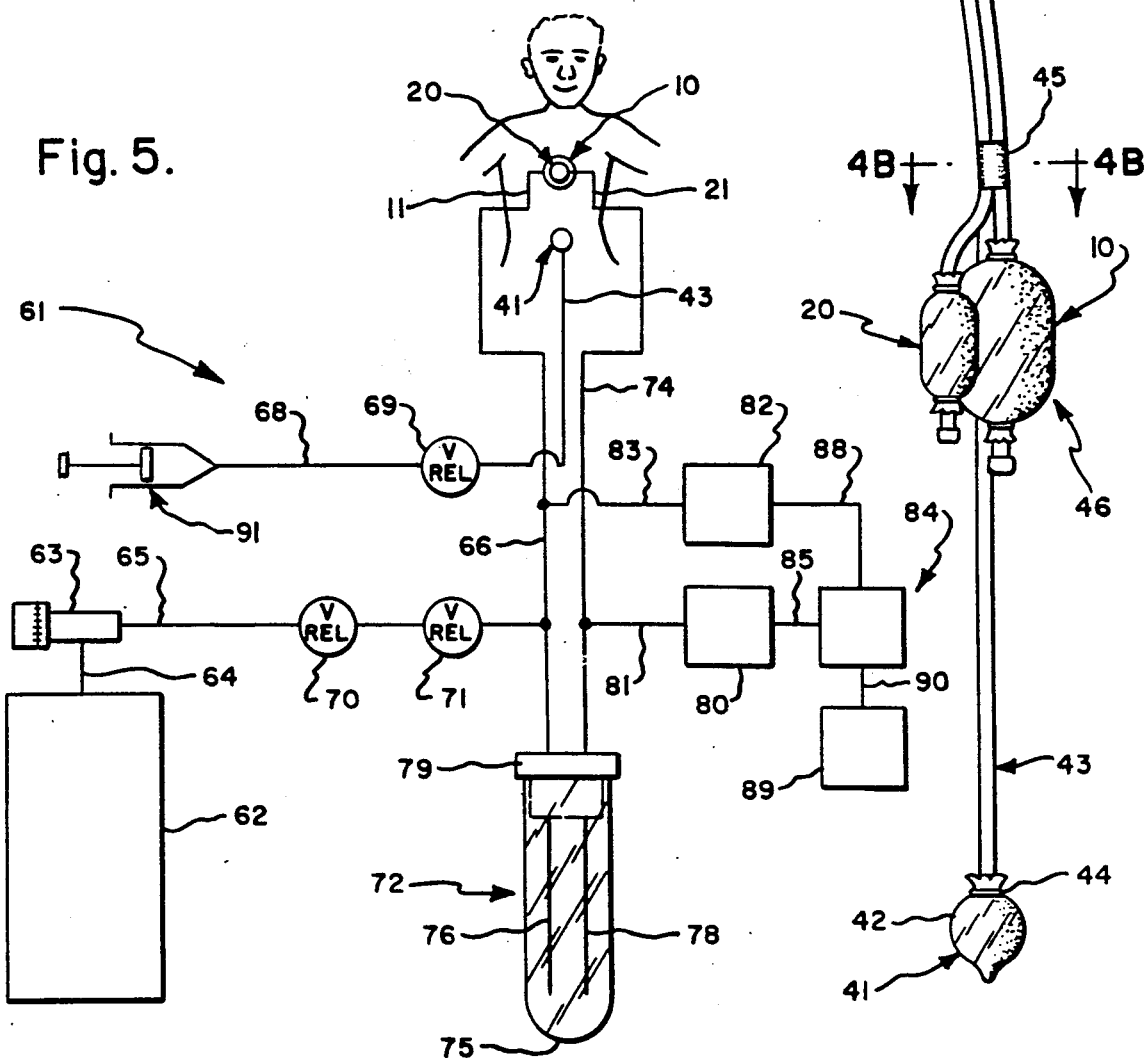

Fig. 7A.
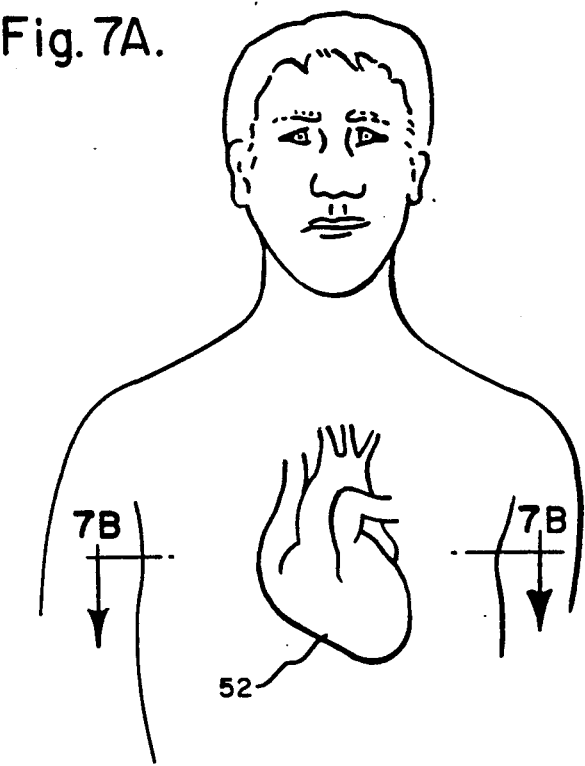
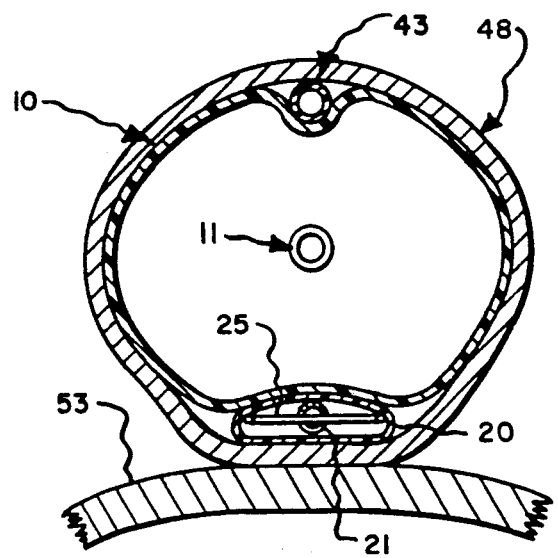
Fig. 7D.
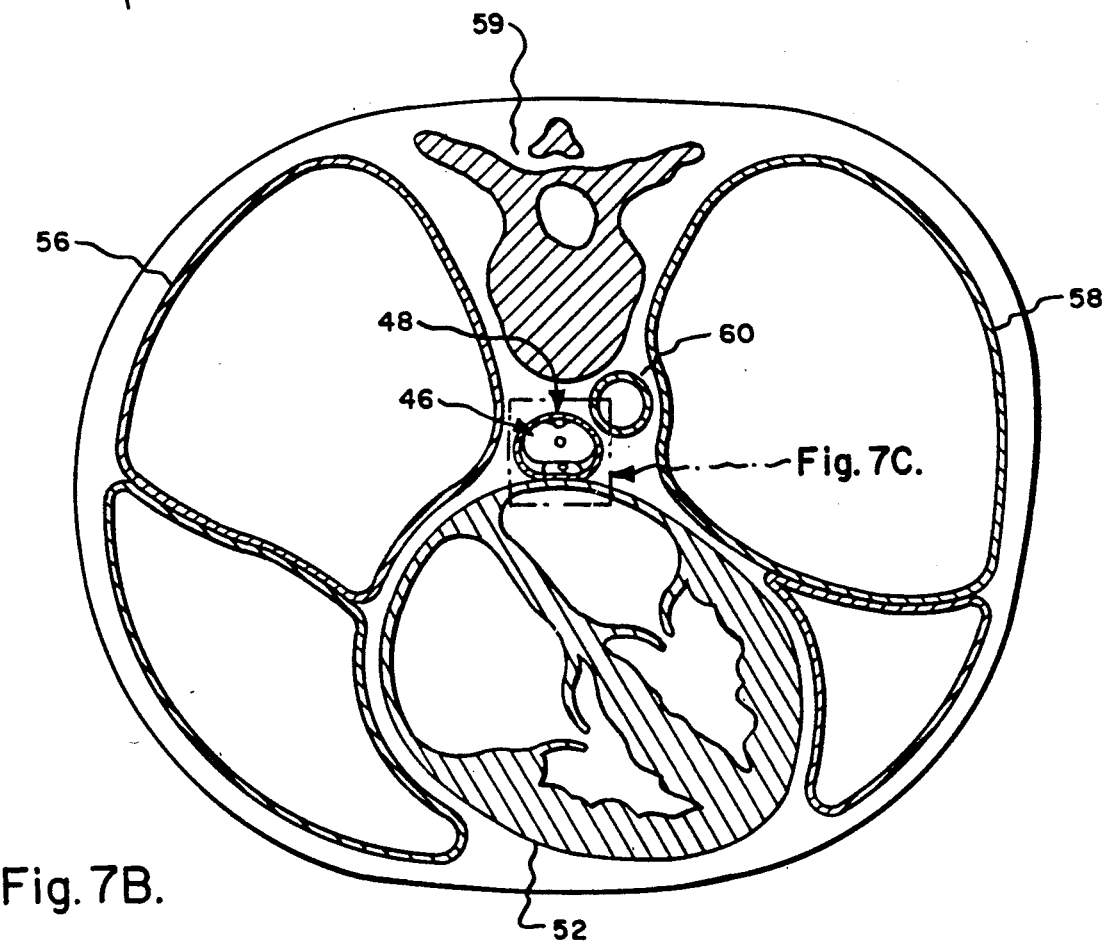
Fig. 7B.

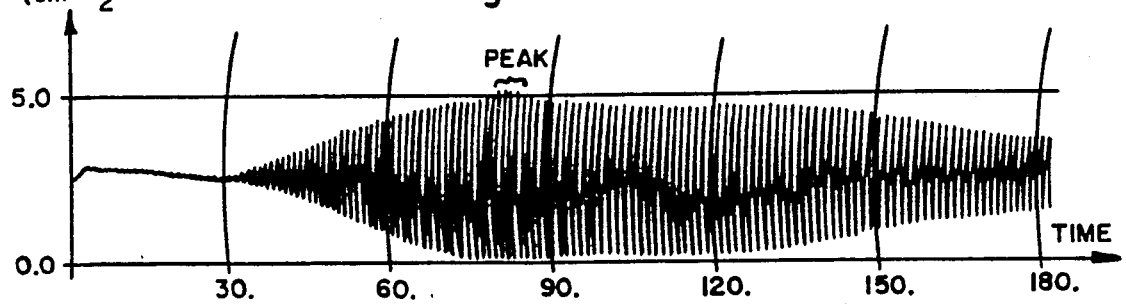
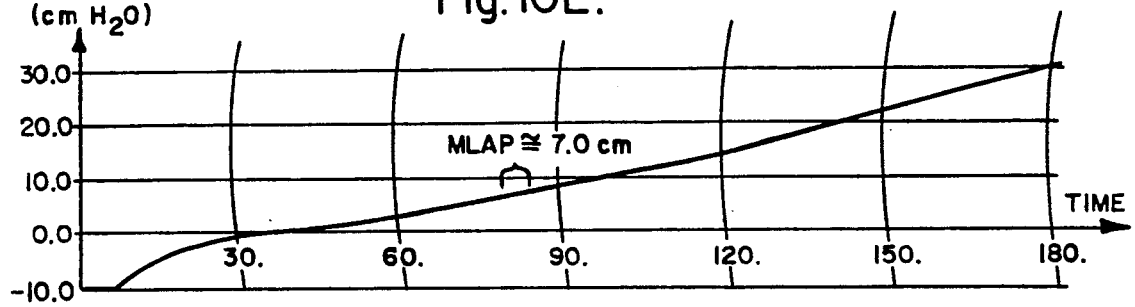
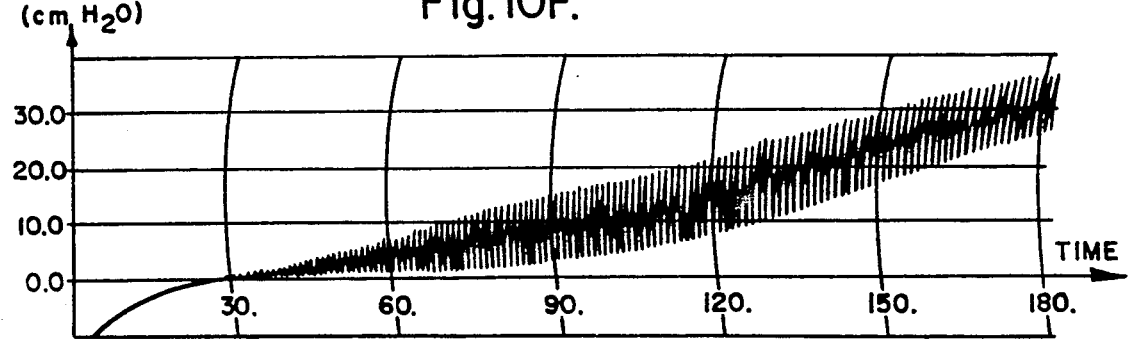
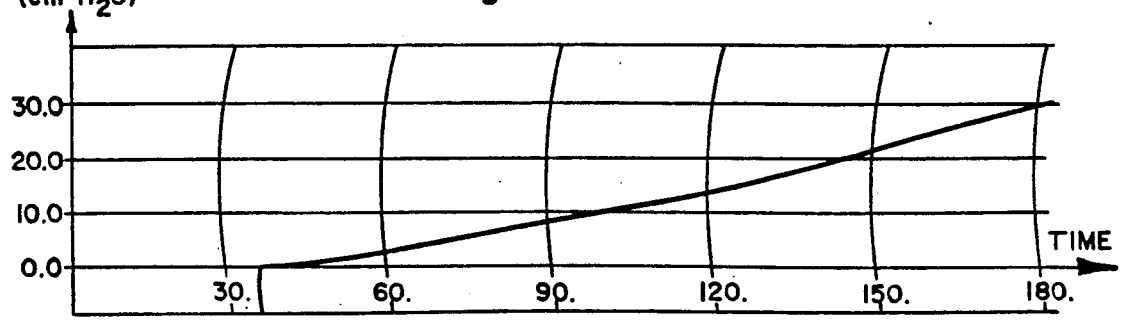

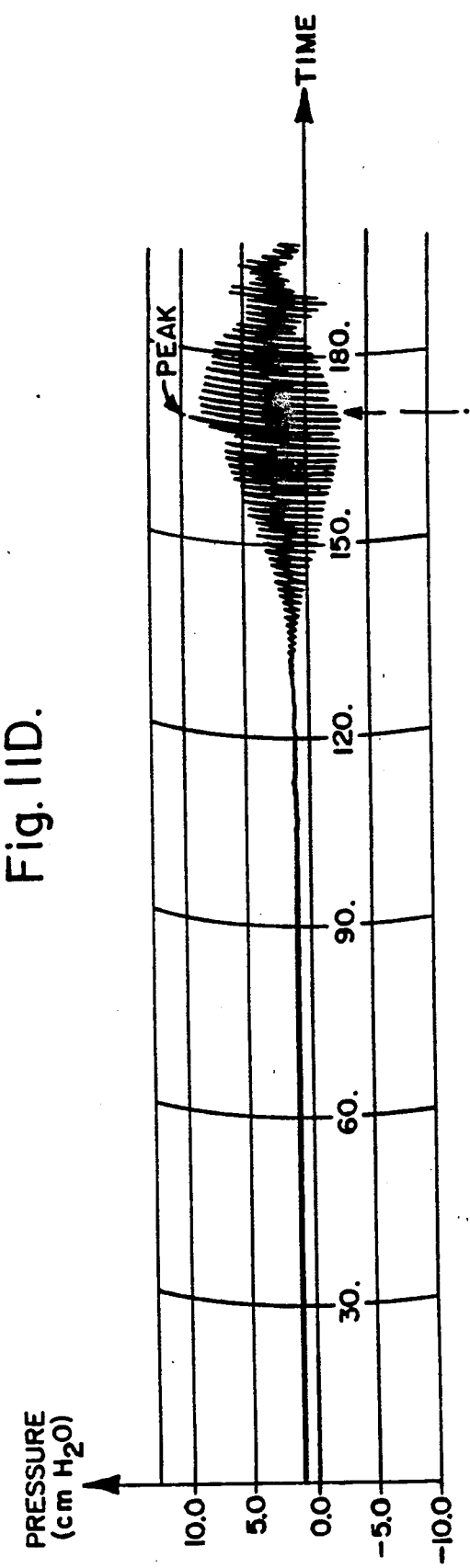
Fig. IID.
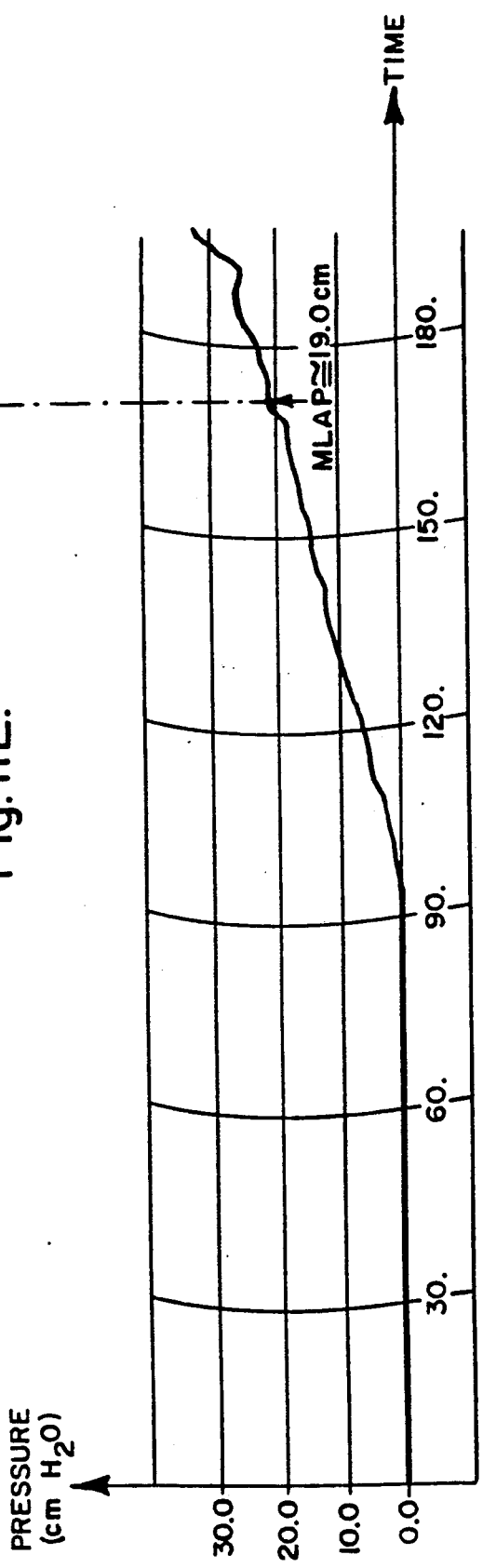
Fig. IIE.

METHOD AND APPARATUS FOR MEASURING BLOOD PRESSURE

FIELD OF THE INVENTION

The present invention relates generally to the measurement of blood pressure and, more specifically, to the indirect measurement of blood pressure. Even more specifically, the invention relates to the indirect measurement of mean left atrial pressure in man.

BACKGROUND OF THE INVENTION

Ever since the English scientist Stephen Hales first measured the mean blood pressure of an unanethesized horse in 1733, scientists and physicians have sought better ways to measure blood pressure in man. In general, these efforts and resulting inventions can be classified as either "direct" methods which involve catheterization, or "indirect" methods such as the well-known blood pressure arm cuff, or sphygmomanometer.

INDIRECT METHODS

The instrument most commonly used in the indirect method is a sphygmomanometer, which comprises an inflatable cuff which wraps around the upper arm above the elbow, a rubber bulb to inflate the cuff, and a device to measure the levels of pressure. It is well known that if the cuff is inflated to above systolic pressure, then slowly decompressed, oscillations corresponding to the heart rate will appear in the cuff pressure beginning somewhat above systolic pressure. These oscillations frequently reach a maximum amplitude and then diminish until they are lost. The French physiologist, E. J. Marey, who discovered this phenomenon in 1876, reasoned that the peak amplitude of oscillation was close to mean arterial pressure. This hypothesis was confirmed by later investigators, and various methods of blood pressure determination based on the "oscillometric principle" were subsequently developed.

In 1905, Dr. N. S. Korotkoff proposed an ausculatory method of determining blood pressure. In this method, an arm cuff is inflated until it stops the circulation of blood beyond the cuff. Thereafter, a stethoscope is used to listen to the artery directly beneath the sleeve. Korotkoff hypothesized that the first sounds correspond to maximum pressure whereas minimum pressure occurred when the sounds disappeared. Later laboratory and clinical studies confirmed the accuracy of the ausculatory method, which eventually became universally adopted in clinical medicine.

DIRECT METHODS

Indirect blood pressure measurement techniques have heretofore been inadequate for the management of cardiac pressures in critically ill patients. The reason for this inadequacy is the imprecision of the obtained measurements and the fact that it has simply not been possible to accurately indirectly measure pulmonary capillary wedge pressure.

In 1953, Lategola and Rahn developed the flow directed pulmonary artery catheter and first demonstrated its efficacy for the direct measurement of pulmonary artery pressure. Lategola and Rahn, *A Self-Guiding Catheter for Cardiac and Pulmonary Arterial Catheterization and Occlusion*, 84 Proc. Soc. Exp. Biol. Med. 667–668 (1953). In 1970, Swan, Ganz and associates first reported use of a flow-directed catheter in humans and further refined it for clinical use and for the measurement of pulmonary capillary wedge pressure. Swan, Ganz, Forrester, Marcus, Diamond and Chonette, *Catheterization of the Heart in Man With Use of a Flow-Directed Balloon-Tipped Catheter*, 283:9 The New England J. Med. 447 (1970). At present, this catheter is an invaluable aid in the management of critically ill patients with pulmonary and cardiac disease, and the pulmonary wedge pressure (as an estimation of left ventricular filling pressure) is the standard of reference for intravascular volume management.

Numerous potential indications for pulmonary artery catheterization are now accepted. For example, catheterization is now widely used in the evaluation and management of patients with acute myocardial infarction, for patients in shock when the cause is not readily apparent, in the recognition of hypovolemia, and in the treatment of patients suffering respiratory failure of uncertain cause with persistent hypoexemia. Catheterization is especially useful in assessing cardiac function in surgical patients, both pre-, intra-, and postoperatively. Indeed, since 1970, the ability to measure pulmonary capillary wedge pressure and cardiac output with the flow-directed catheter has resulted in the development of bedside hemodynamic monitoring, a procedure now performed daily in most hospitals in the United States. J. M. Gore et al., *Handbook of Hemodynamic Monitoring*, 3 (1985). In fact, since the introduction of the Swan-Ganz catheter in 1970, several million pulmonary catheters have been placed in patients with acute myocardial infarction. Gore et al., 92:4 Chest, 712 (October 1987).

Despite the widespread use of the pulmonary artery flow-directed catheter, the procedure is not without drawbacks. Complications that may arise from use of the catheter include pulmonary artery thrombosis or embolus, knotting of the catheter, rupture of the balloon and/or of a pulmonary artery, pulmonary hemorrhage, right atrial thrombosis, sepsis, internal jugular stenosis or thrombosis, atrial and ventricular arrhythmias, electromechanical dissociation, right-sided endocardial lesions, and right-sided endocardial infection. Robin, *The Cult of the Swan-Ganz Catheter, Overuse and Abuse of Pulmonary Flow Catheters*, 103:3 Annals of Internal Medicine 445 (September 1985).

In recent years, the safety and efficacy of pulmonary artery catheterization has become a subject of increased scrutiny and concern. One study suggests that flow-directed pulmonary artery catheterization may predispose patients to the development of right-sided endocarditis. Rowley, Clubb, Smith and Cabin, *Right-Sided Infective Endocarditis as a Consequence of Flow-Directed Pulmonary-Artery Catheterization*, 311:18 The New England J. Med. 1152 (Nov. 1, 1984). In fact, the medical literature abounds with articles addressing the numerous medical complications associated with pulmonary artery catheterization (for a sampling of pertinent references, see, e.g., Murray, *Complications of Invasive Monitoring*, 15:2 Medical Instrumentation 85 at p. 89 (March–April 1981). Another significant concern involves the relatively high fiscal cost of critical care invasive monitoring, which cost would be minimized by the availability of a non-invasive procedure where indicated. Perhaps the most serious allegation to date is that complications associated with the use of the pulmonary artery catheter in patients with acute myocardial infarction have resulted in an unusually and unacceptably high mortality rate. Robin, *Death by Pulmonary Artery*

*Flow-Directed Catheter (editorial), Time for a Moratorium?*, 92:4 Chest 727 (October 1987). Thus, a need has existed for a non-invasive and less costly method for measuring mean left atrial pressure in man.

Hemodynamic measurement remains an important and feasible adjunct to clinical practice. Successful monitoring permits accurate determination of the state of the diseased heart, and provides guidance for treatment and intervention to alter the course of a variety of diseases. In view of the recent explosion of medical literature questioning the efficacy and safety of pulmonary artery catheterization, the benefits are clearly not without substantial costs. It is recognized that modern Swan-Ganz catheters allow for the measurement of cardiac output, oxygen consumption, continuous mixed venous oxygen saturation determination and cardiac pacemaking, and that many critically ill patients will require this degree of sophisticated monitoring. Nevertheless, there are numerous patients who could be safely managed in intermediate care units or on regular nursing floors given the knowledge of mean left atrial pressure alone. Certain patients undergoing general anesthesia could also benefit from less invasive monitoring of mean left atrial pressures. Furthermore, a simplified technique for the measurement of mean left atrial pressure could be used to rationally screen patients to determine whether or not they would benefit from Swan-Ganz catheterization; otherwise, simple monitoring of mean left atrial pressure by the present invention may suffice to manage the patient outside the intensive care setting.

Heretofore, a long-felt need has existed for an alternative method of measuring mean left atrial pressure. This is the underlying objective of the present invention.

SUMMARY OF THE INVENTION

The present invention generally provides a method for measuring left atrial pressure by inserting a sensing probe into the esophagus and positioning the probe so that pressure from the left atrium is sensed by the probe. More particularly, the invention provides a method for measuring left atrial pressure by inserting a balloon-containing catheter into the esophagus and positioning the catheter so that when the balloon is inflated, pressure from the left atrium affects the balloon; inflating the balloon; and, determining the left atrial pressure by the effect of the atrial pressure upon the balloon. Apparatus for carrying out the method is also disclosed, comprising a balloon-containing catheter adapted to be insertable into an esophagus; means for positioning the balloon-containing catheter in the esophagus such that when the balloon is inflated, pressure from the left atrium affects the balloon; means for inflating the balloon; and, means for determining the left atrial pressure by the effect of the atrial pressure upon the balloon.

Accordingly, a primary object of the present invention is to provide a safe, accurate and reliable non-invasive method and apparatus for the measurement of mean left atrial pressure in man.

A secondary object of the present invention is to provide an economical method and apparatus for the measurement of mean left atrial pressure in man.

A further object of the invention is to provide a method of measuring left atrial pressure which may be administered by non-physicians.

BRIEF DESCRIPTION OF THE DRAWINGS

FIG. 1A is an exploded view of the counter-pressure balloon-containing catheter of the invention.

FIG. 1B is a partial sectional side view of the counter-pressure balloon-containing catheter shown in FIG. 1A in an uninflated state.

FIG. 1C is a partial sectional side view of the counter-pressure balloon-containing catheter shown in FIG. 1B in an inflated state.

FIG. 1D is a cross-sectional view of the inflated balloon-containing catheter of FIG. 1C taken at plane A—A'.

FIG. 2A is an exploded view of the isovolumetric balloon-containing catheter of the invention.

FIG. 2B is a partial sectional side view of the isovolumetric balloon-containing catheter of FIG. 2A in an uninflated state.

FIG. 2C is a partial sectional top view of the isovolumetric balloon-containing catheter of FIG. 2A in an inflated state.

FIG. 2D is a partial sectional side view of the isovolumetric balloon-containing catheter of FIG. 2A in an inflated state.

FIG. 2E is a cross-sectional view of the balloon-containing catheter shown in FIG. 2D taken at plane B—B'.

FIG. 3A is an exploded view of the flutter-valve balloon-containing catheter of the invention.

FIG. 3B is a partial sectional side view of the flutter-valve balloon-containing catheter shown in an uninflated state.

FIG. 3C is a partial sectional top view of the flutter-valve balloon-containing catheter of the invention.

FIG. 3D is a cross-sectional view of the flutter-valve balloon-containing catheter shown in FIG. 3C taken at plane D—D'.

FIG. 4A is a perspective view of a first embodiment of the invention comprising the combination of an isovolumetric balloon-containing catheter, a counter-pressure balloon-containing catheter, and a positioning balloon-containing catheter.

FIG. 4B is a cross-sectional view of the catheters shown in FIG. 4A taken at plane C—C'.

FIG. 5 is a schematic representation of a first embodiment of the invention utilizing the counter-pressure and isovolumetric balloon-containing catheters.

FIG. 7A is a front sectional view of the human body illustrating the relative position of the heart.

FIG. 7B is a top cross-sectional view of the human body taken along horizontal plane D—D' as shown in FIG. 7A at the level of the eighth thoracic vertebra.

FIG. 7C is a cross-sectional view of the esophagus showing the relative positioning of the isovolumetric balloon-containing catheter, the counter-pressure balloon-containing catheter and the catheter of the positioning balloon.

FIG. 7D is an enlarged view of FIG. 7C.

FIG. 8A is a perspective view of a second embodiment of the invention comprising the combination of a flutter-valve balloon-containing catheter, a counter-pressure balloon-containing catheter, and a positioning balloon-containing catheter.

FIG. 8B is a cross-sectional view of the catheters shown in FIG. 8A taken at plane E—E'.

FIGS. 10A-10G represent typical test results obtained with a first embodiment of the invention comprising a combination isovolumetric-counter pressure balloon-containing catheter.

FIG. 10A shows the absolute heart simulator pressure similar to that which could be expected to be measured in a human subject.

FIG. 10B shows the mean heart simulator pressure derived from the absolute pressure of FIG. 10A.

FIG. 10C depicts the absolute pressure in the isovolumetric balloon-containing catheter as the balloon is slowly inflated.

FIG. 10D illustrates a steady baseline, increased gain representation of the signal of FIG. 10C, obtained by inverting the signal of FIG. 10E, adding the inverted signal to the original signal and amplifying the result.

FIG. 10E represents the mean pressure of the waveform shown in FIG. 10C.

FIG. 10F represents the absolute pressure within the counter-pressure balloon.

FIG. 10G represents the mean pressure within the counter-pressure balloon, which is derived from the waveform of FIG. 10F.

FIGS. 11A-11E represent typical test results obtained with a second embodiment of the invention comprising a flutter-valve catheter.

FIG. 11A represents the absolute pressure of the simulation heart.

FIG. 11B is the mean pressure of the signal of FIG. 11A.

FIG. 11C represents the absolute pressure within the flutter-valve balloon.

FIG. 11D is a steady baseline, increased gain representation of the signal of FIG. 11C, obtained by inverting the signal of FIG. 11E, adding the inverted signal to the original signal and amplifying the result. FIG. 11E represents the mean pressure of the waveform shown in FIG. 11C.

FIG. 12A illustrates the trace obtained with a balloon volume of 1 mL.

FIG. 12B illustrates the trace obtained with a balloon volume of 2 mL.

FIG. 12C illustrates the trace obtained with a balloon volume of 3 mL.

FIG. 12D illustrates the trace obtained with a balloon volume of 3.5 mL.

DETAILED DESCRIPTION OF THE INVENTION

Figure 6:
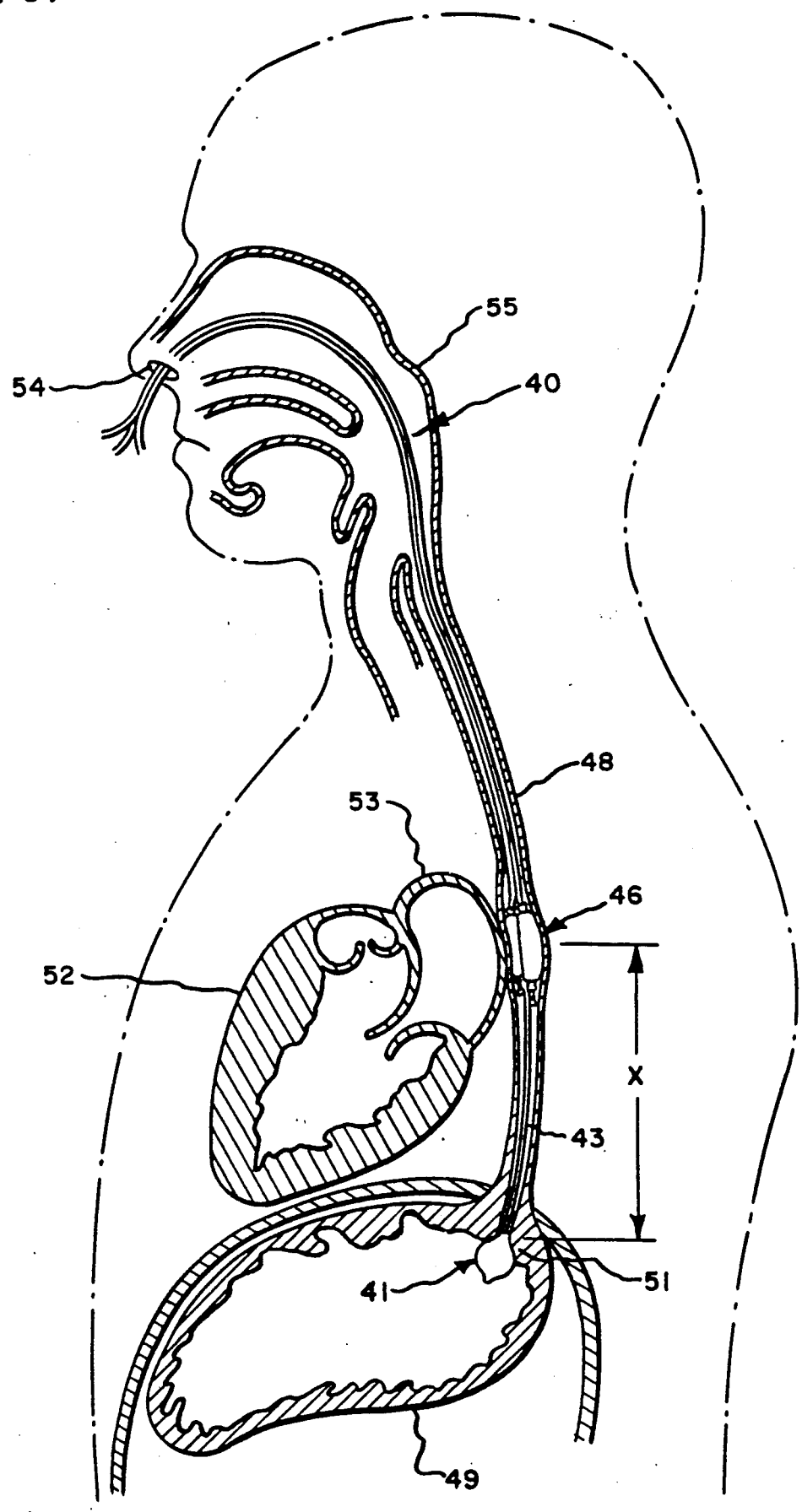
FIG. 6 is a left lateral sectional view of the human body taken along the mid-sagittal plane and showing the location of the sensing catheter within the esophagus and the positioning balloon within the stomach.

At the outset, it should be clearly understood that the drawings are intended to be read together with the specification, and are to be considered a portion of the entire "written description" of this invention, as required by 35 U.S.C. Section 112. Also, like numerals of different drawing figures refer to the same element. It should also be understood that the drawings depict only a first and second embodiment of the invention. Although the drawings depict the best mode of the invention, they in no way illustrate the only way in which the invention may be practiced. For example, a first embodiment utilizes a "sensing" probe comprising two balloon-containing catheters, and a second embodiment utilizes a "sensing" probe comprised of a single balloon-containing catheter. Both embodiments utilize a positioning balloon-containing catheter as well. However, it is readily apparent to those having ordinary skill in the art to which the invention pertains that any number and/or combination of balloon-containing catheters may suffice and achieve the intended objective of the invention. The claims are not intended to be limited in scope to a specific embodiment but rather are directed to the general concept of measuring left atrial pressure using an esophageal balloon-containing catheter.

DESCRIPTION OF A FIRST EMBODIMENT

FIG. 1A is an exploded view of the counter-pressure balloon-containing catheter 10 of the invention. Catheter 10 includes first catheter 11 having a first section 12 and a second section 13. Counter-pressure balloon 14 is secured to first section 12 and second section 13 by securing means 15, shown in FIG. 1A as nylon surgical thread. Balloon 14 is also cemented to first and second sections 12 and 13, respectively, to seal the balloon and prevent the leakage of gas from the balloon-catheter interface. Endcap 16 is cemented to the distal end of second section 13 to prevent the escape of gas therefrom.

Suitable catheters are made from flexible, chemically inert, non-toxic materials such as polyvinyl chloride. Suitable catheters can withstand operating pressures without significant expansion. Although other catheters will work satisfactorily, a preferred embodiment catheter for use in the invention is a Tygon ® brand catheter constructed of polyvinyl chloride tubing having an inner diameter of approximately 0.050" (available from Cole-Parmer Instrument Co., 7425 N. Oak Park Avenue, Chicago, Ill. 60648-9930, as shown on page 636 of the Cole-Parmer 1989-90 Catalog).

Balloons may be constructed of any flexible, non-toxic film which can withstand operating pressures without rupture or irreversible deformation. Such balloons may, for example, be constructed of low density polyethylene film. In a preferred embodiment, balloons are constructed of Extrel ® SF brand polyethylene film (available from Exxon Chemical Co., Polymers Group, Division of Exxon Corp., 351 N. Oakwood Road, Lake Zurich, Ill. 60047-1562).

Although the dimensions of balloon 14 may vary, in a preferred embodiment, balloon 14 has a generally irregular shape when uninflated, and is open at both ends for mating with first opening 18 and second opening 19 of first section 12 and second section 13, respectively, of catheter 11, and has a diameter of approximately 1.5 centimeters and a length of approximately 2.0 centimeters. When inflated, balloon 14 takes on a generally cylindrical shape (as shown in FIG. 1D) and, in a preferred embodiment, is inflated to a volume of approximately 4 milliliters.

FIG. 1B is a partial sectional side view of counter-pressure balloon-containing catheter 10 shown in FIG. 1A in an uninflated state, and further illustrates the generally irregular shape of balloon 14. FIG. 1B also illustrates securing means 15 which tie balloon 14 to catheter 11.

FIG. 1C is a partial sectional side view of counter-pressure balloon-containing catheter 10 as shown in FIG. 1B, except in an inflated state.

FIG. 1D is a cross sectional view of inflated balloon-containing catheter 10 as shown in FIG. 1C taken at plane A—A'.

FIG. 2A is an exploded view of the isovolumetric balloon-containing catheter 20 of the invention. Catheter 20 includes second catheter 21 having notch 24 and isovolumetric balloon 28. Isovolumetric balloon 28 is comprised of outer membrane 22 which, in a preferred embodiment, is formed of low density polyethylene film. Balloon 28 also includes inner support structure 25 which, in a preferred embodiment, is stainless steel wire having an outer diameter of 0.025 inches. Support structure 25 is oval in shape and fits snugly within notch 24 of catheter 21. Membrane 22 encapsulates support structure 25 and catheter 21 and is secured to catheter 21 outside the ends of notch 24 by securing means 26, shown in FIG. 2A as nylon surgical thread. Membrane 22 is also cemented to catheter 21 at both ends to seal the balloon and prevent the leakage of gas from the balloon-catheter interface. Endcap 29 is cemented to the distal end of catheter 21 to prevent the escape of gas therefrom. As shown in FIG. 2A, membrane 22 has a seam 30 where the ends of a piece of polyethylene film are welded. Thus, membrane 22 has a generally cylindrical shape before being placed about second catheter 21. However, as shown in FIG. 2E, contact with support structure 25 causes isovolumetric balloon 20 to take on a generally oval or elliptical cross-sectional shape. This cross-sectional shape for isovolumetric balloon 20 is highly preferable to maximize surface area contact between the balloon and the wall of the esophagus.

FIG. 2B is a partial sectional side view of isovolumetric balloon-containing catheter 20 shown in FIG. 2A in an uninflated state, and also illustrates securing means 26 which tie membrane 22 to catheter 21.

FIG. 2C is a partial sectional top view of the balloon-containing catheter shown in FIG. 2B.

FIG. 2D is a partial sectional side view of isovolumetric balloon-containing catheter 20 as shown in FIG. 2B, except in an inflated state. It is important to note that balloon volume before and after inflation is about the same, i.e., the balloon is isovolumetric.

FIG. 2E is a cross sectional view of inflated balloon-containing catheter 20 as shown in FIG. 2D taken at plane B—B'.

FIG. 4A is a perspective view of a first embodiment of the invention. Balloon-containing sensing probe 40 comprises isovolumetric balloon-containing catheter 20, counter-pressure balloon-containing catheter 10, and positioning balloon-containing catheter 41, where catheters 10 and 20 combined form the sensing catheter. Positioning balloon-containing catheter 41 includes positioning balloon 42 which is secured to tethering catheter 43 via securing means 44 which may comprise tied surgical thread in combination with silicone cement. Positioning balloon 42 is formed of low density polyethylene film. Catheter 43 is comprised of polyvinyl chloride tubing. As shown in FIGS. 4A and 4B, catheters 11, 21 and 43 are held together by securing means 45 which may, for example, comprise epoxy cement held in place about the catheters by surgical tape. Alternatively, a tri-lumen catheter of pre-formed polyvinyl chloride may be used.

FIGS. 6 and 7 illustrate the placement of balloon-containing sensing probe 40 within the human body. FIG. 6 is a left lateral sectional view of the human body taken along the mid-sagittal plane and showing the location of sensing probe 40 (isovolumetric balloon-containing catheter 20 and counter-pressure balloon-containing catheter 10) within the esophagus 48 and positioning balloon-containing catheter 41 within the stomach 49. In practice, positioning balloon-containing catheter 41 is inserted through nasal passage 54, pharynx 55, esophagus 48 and into the stomach 49. Catheter 41 includes tethering catheter 43 which is tied to balloons 46 at a predetermined distance "x" from the positioning balloon to the balloon of the balloon-containing catheter. Balloons 46 refer to the balloons of isovolumetric catheter 20 and counter-pressure catheter 10. Predetermined distance "x" corresponds approximately to the relatively constant distance in man between the esophago-gastric junction 51 and the left atrium 53 of heart 52 (see, e.g., H. R. Andersen and P. Pless, *Trans-Esophageal Pacing*, 6 PACE 674 (July-August 1983)). The positioning balloon is inflated to a sufficient size (approximately 8 mL volume) such that it will not pass through the esophago-gastric junction. Gentle traction is applied at the nose to the tethering catheter to keep sensing balloons 46 in position in the esophagus proximate left atrium 53.

In addition to proper longitudinal position of the catheter within the esophagus, rotational position is also critical. To ensure proper rotational position, several methods may be used. First, satisfactory results are obtained by beginning the measurement process while slowly manually rotating or twisting the sensing catheter at the patient's nose, causing the catheter to rotate within the esophagus. One having ordinary skill in the art can monitor the measured pressures and determine when the sensing catheter is properly positioned. For example, if the catheter is positioned such that the sensing catheter is displaced 180 degrees from the left atrium, the pressure signals will be greatly attenuated, irregular, or even non-existent. Conversely, the strongest signals will occur when the sensing catheter is positioned proximate the left atrium. An alternative and suggested method for ensuring proper rotational position is to use a sensing catheter having one or two embedded rigid wires included therein. The rigid wires will minimize inadvertent rotation of the sensing catheter as it is inserted through the patient's nose and into the esophagus. Yet another alternative would be to wrap the sensing catheter around the counter-pressure balloon, thus ensuring that the sensing catheter would always be in contact with the esophageal wall. Finally, it should be noted that although the catheters of the invention are shown as inserted through the patient's nose, insertion through the mouth is equally satisfactory.

FIG. 7A is a front sectional view of the human body illustrating the relative position of the heart. FIG. 7B is a top cross-sectional view of the human body taken along horizontal plane D—D' as shown in FIG. 7A at the level of the eighth thoracic vertebra. In general, FIG. 7B shows heart 52, right lung 56, left lung 58, aorta 60, esophagus 48, and vertebral column 59. As shown in FIGS. 6 and 7D, left atrium 53 is proximate esophagus 48. In fact, as shown in enlarged view in FIG. 7D, the outer esophageal wall is essentially in direct contact with the outer wall of left atrium 53. FIG. 7D shows the relative position in the esophagus of counter-pressure balloon-containing catheter 10, isovolumetric balloon-containing catheter 20, and tethering catheter 43.

FIG. 5 illustrates a schematic representation 61 of the first embodiment of the invention, and is particularly useful in understanding the method of the invention. Prior to commencing the pressure measurements utilizing the apparatus depicted in FIG. 5, the entire system should be brought under a vacuum. In other words, all catheters and balloons, and condenser 72 should be purged of compressed gas prior to beginning a new measurement. This ensures consistency, accuracy and reliability of pressure measurements by removing residual gas from the system.

As mentioned previously, once the catheters have been inserted into the esophagus and stomach, a preliminary step in the method is to properly position the esophageal catheters. For this purpose, positioning balloon 42 (part of positioning catheter 41) is filled with gas via positioning catheter 43 which fills with gas from supply line 68 when relief valve 69 is open. Gas to fill balloon 42 is provided by fixed-volume syringe 91. Although proper selection of syringe 91 ensures against over-filling of balloon 42, safety relief valve 69 provides added safety, in that catheter 43 and balloon 42 may be vented to the atmosphere in the event of dangerously high pressure, such as would cause balloon 42 to rupture. In a preferred embodiment syringe 91 provides a source of gas for filling balloon 42, although it is readily apparent that other filling means would also be suitable. For example, with proper metering valves, balloon 42 could be filled directly from nitrogen tank 62.

Once balloon-containing catheter 41 is filled to a volume sufficient to prevent its passage out of the stomach and into the esophagus, gentle traction is applied at nasal passage 54 (shown in FIG. 6) to properly position sensing balloons 46 proximate the left atrium 53. Once the sensing balloons have been properly positioned, individual catheters 10 and 20 may be filled and the mean left atrial pressure measured.

As shown in FIG. 5, a source of compressed gas 62 supplies gas via supply line 64 and metering valve 63 to main metered supply line 65. In a preferred embodiment, nitrogen gas is used at a relatively constant pressure of approximately 62.0 psi. Of course, other non-poisonous gases are also suitable, as are other pressures. Also in a preferred embodiment, valve 63 is a Nupro ® brand needle valve (micrometer valve) which is designed to allow a broad range of near constant flow rates against back pressures to a maximum of 50 cm H₂O (0.74 psi). In a best mode, both isovolumetric catheter 20 and counter-pressure catheter 10 are filled at the same rate of approximately 2 to 4 mL/minute, although other flow rates are also suitable. The rate of inflation is regulated to maintain approximately equal pressures in both catheters 10 and 20 at all times. Also, the pressure of the gas in first catheter 11 and second catheter 21 (FIG. 4A) is gradually increased to a maximum pressure of approximately 50 cm H₂O.

Counter-pressure catheter 10 is filled via line 66 (equivalent to first catheter 11 in FIG. 4A) when pressure relief valves 70 and 71 are open. Isovolumetric catheter 20 is filled via line 74 (equivalent to second catheter 21 in FIG. 4A) which is fed compressed gas through condenser 72. It is important to note that the volume of balloon-containing catheter 20 remains relatively constant even while being filled and throughout the measuring process. Condenser 72 comprises 12 mL closed test tube 75 having end stopper 79 through which two 1½" 27 gauge needles 76 and 78 protrude. Gas is introduced to condenser 72 via needle 76 which communicates gas via line 66 when valves 70 and 71 are open. Of course, the flow rate of gas in line 66 is controlled by metering valve 63 which regulates flow to main supply line 65. Compressed gas leaves condenser 72 via needle 78 to fill isovolumetric catheter 20 via line 74. Condenser 72 functions as a capacitance chamber or low pass filter and impedance which isolates the pressure waveform in the counter-pressure balloon from that in the isovolumetric balloon while allowing both balloons to fill at nearly the same mean pressure. Condenser 72 also functions to dampen the pressure responses from both catheters 10 and 20 so as to attenuate any cross-talk therebetween. Pressure transducer 80 senses the pressure in isovolumetric catheter 20 via line 81, and converts the pressure signal to an electrical signal which is communicated to processing circuit 84 via line 85. Similarly, pressure transducer 82 senses the pressure in counter-pressure catheter 10 via line 83, and converts the pressure signal to an electrical signal which is communicated to processing circuit 84 via line 88. Processing circuit 84 is a conventional electronic signal processing circuit which processes and conditions the electrical signal representations of pressure, and communicates these signals to display means 89 via line 90. Display means 89 may be a digital display, a strip chart recorder, a CRT, or any suitable device for displaying the measured pressures.

DESCRIPTION OF A SECOND EMBODIMENT

Figure 9:
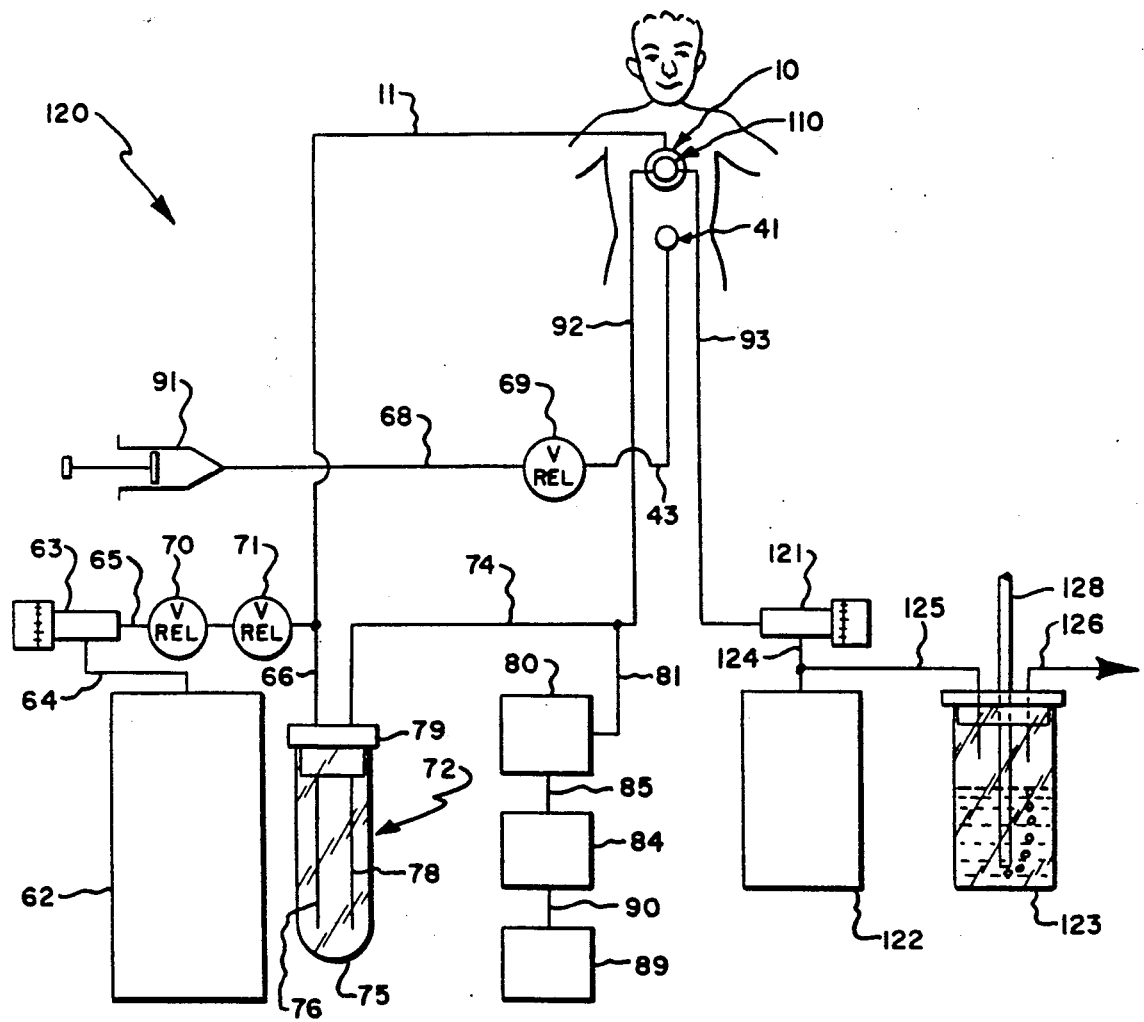
FIG. 9 is a schematic representation of a second embodiment of the invention utilizing the flutter-valve and counter-pressure balloon-containing catheters.

FIGS. 3, 8 and 9 depict a second embodiment of the invention. This second embodiment utilizes a single flutter-valve balloon-containing catheter as a sensing catheter to determine mean left atrial pressure. Similarly to the aforedescribed first embodiment, a counter-pressure balloon is also utilized in the second embodiment to ensure proper positioning of the sensing catheter (flutter-valve catheter) within the esophagus. Unlike the first embodiment, however, the counter-pressure balloon-containing catheter of the second embodiment is not part of the pressure "sensing" catheter, i.e., the pressure within the counter-pressure catheter is not sensed or required to determine mean left atrial pressure.

FIG. 3A is an exploded view of the flutter-valve balloon-containing catheter 100 of the invention. Catheter 100 includes inlet catheter 92 and exhaust catheter 93. Flutter-valve balloon 95 is secured to catheters 92 and 93 by securing means 96, shown in FIG. 3A as nylon surgical thread. Balloon 95 is also cemented to catheters 92 and 93, respectively, e.g., with silicone cement, to seal the balloon and prevent the leakage of gas from the balloon-catheter interface. Balloon 95 is constructed of polyethylene film. Although the dimensions of balloon 95 may vary, in a preferred embodiment, balloon 95 has a length of approximately 35 millimeters and a collapsed width of approximately 4 millimeters. The polyethylene film of balloon 95 is approximately 0.0005" in thickness. When fully inflated, balloon 95 takes on a generally cylindrical shape (as shown in FIGS. 3C and 3D) and, in a preferred embodiment, can reach a volume of approximately 0.18 milliliters.

FIG. 3B is a partial sectional side view of the flutter-valve balloon-containing catheter 100 shown in an uninflated state, and illustrates the generally thin shape of balloon 95. FIG. 3B also illustrates securing means 96 which tie balloon 95 to catheters 92 and 93, respectively.

FIG. 3C is a partial sectional top view of flutter-valve balloon-containing catheter 100.

FIG. 3D is a cross-sectional view of balloon-containing catheter 100 as shown in FIG. 3C taken at plane D—D'. FIG. 8A is a perspective view of a second embodiment of the invention. Balloon-containing catheter 110 comprises flutter-valve balloon-containing catheter 100, counter-pressure balloon-containing catheter 10, and positioning balloon-containing catheter 41, where catheter 100 functions as the sensing catheter. Positioning balloon-containing catheter 41 includes positioning balloon 42 which is secured to tethering catheter 43 via securing means 44 which may comprise tied surgical thread in combination with silicone cement. Positioning balloon 42 is formed of low density polyethylene film. Catheter 43 is polyvinyl chloride tubing. As shown in FIGS. 8A and 8B, catheters 11, 92, 93 and 43 are held together by securing means 45 which may, for example, comprise epoxy cement held in place about the catheters by surgical tape. Alternatively, a quadlumen catheter of pre-formed polyvinyl chloride may be used.

FIG. 9 is a schematic representation 120 of a second embodiment of the invention. As in the first embodiment, the catheters are inserted into the esophagus and stomach, and then properly positioned before commencing the measurements.

As shown in FIG. 9, many of the components of the system are identical to those of the first embodiment, as denoted by corresponding reference numerals in FIGS. 5 and 9. It should be readily apparent that the major differences between the first and second embodiments are the substitution of a flutter-valve catheter 100 for isovolumetric catheter 20, the elimination of a pressure transducer for the counter-pressure catheter, and the addition of exhaust equipment 121, 122 and 123 to maintain a regulated vacuum and/or back pressure on the exhaust line of the flutter-valve catheter, and to regulate exhaust flow, which is necessary for accurate flutter-valve performance. Also, since only the flutter-valve balloon is used to sense the left atrial pressure, counter-pressure balloon 10 may be filled independently (i.e., at a different filling rate and pressure) with respect to flutter-valve balloon 100.

Prior to commencing pressure measurements, and prior to filling catheters 10 and 100 with gas, flutter-valve catheter 100 is brought under a vacuum. Experiments indicate that the system vacuum required is a negative pressure below the minimum expected pressure to be measured. For example, typical pressure measurements in the thoracic region can be expected to vary from approximately −10 cm H$_2$O to +10 cm H$_2$O. Therefore, an initial vacuum of approximately −12 cm H$_2$O would be sufficient. In a preferred second embodiment, a vacuum is created by components 121, 122 and 123. Vacuum regulator 123 is a graduated vessel partially filled with water and sealed by a top cap. Tube 128 extends through the top cap enabling air from the atmosphere to enter the vessel. Suction line 126 is connected to a standard sink eductor (not shown) which operates according to Venturi's principle to create a vacuum within regulator 123. The strength of the vacuum created may be regulated by increasing or decreasing the flow rate of water flowing through the sink eductor. As air is educted from regulator 123 via line 126, air is sucked into the vessel from the atmosphere via tube 128, creating air bubbles in the water as shown. Regulator 123 also causes a vacuum to exist in lines 124 and 125 and, when metering valve 121 is open, in exhaust catheter 93 and flutter-valve catheter 100 as well. Small oscillations in pressure caused by pressure regulator 123 are dampened and isolated from pressure transducer 80 by vacuum capacitance chamber 122. Chamber 122 functions to ensure that only the pure pressure exerted by the left atrium on flutter-valve catheter 100 will be sensed by transducer 80.

Once a stable vacuum lower than the lowest expected pressure to be measured has been achieved, a measuring test run can commence. Nitrogen gas is slowly allowed to fill counter-pressure balloon-containing catheter 10 via line 66 (equivalent to first catheter 11 in FIG. 4A) when pressure relief valves 70 and 71 are open. Flutter-valve catheter 100 is simultaneously slowly filled via line 74 (equivalent to catheter 92 in FIG. 8A) which is fed compressed gas through condenser 72 to balloon-containing catheter 110 as previously described with respect to balloon type catheter 20. Compressed gas leaves condenser 72 via needle 78 to fill flutter-valve catheter 100 via line 74, which enters inlet catheter 92. Initially, gas is metered through flutter-valve 100 at a very low flow rate of approximately 0.2 mL/min. and then uniformly increased over time to a maximum flow rate of approximately 4.0 mL/min. This causes the mean pressure in the flutter-valve balloon to slowly increase, as do the imposed peak to trough pressures, and the system typically resonates at the point where the mean pressure in the flutter-valve balloon equals the mean driving pressure of the left atrium. It is this mean pressure which the invention seeks to determine.

Averting again to FIG. 9, condenser 72 functions as a capacitance chamber as previously described with respect to the first embodiment. Pressure transducer 80 senses the pressure in flutter-valve catheter 100 via line 81, and converts the pressure signal to an electrical signal which is communicated to processing circuit 84 via line 85. Processing circuit 84 functions as described in the first embodiment.

ALTERNATIVE EMBODIMENTS

As stated previously, the claims are not intended to be limited in scope to the specific embodiments disclosed herein, but are directed to the general concept of measuring left atrial pressure using an esophageal balloon-containing catheter. One having ordinary skill in the art may readily imagine alternative embodiments which accomplish the same end results. For example, one such embodiment contemplated by the inventor comprises a catheter-mounted transducer in place of the isovolumetric or flutter-valve catheter. This configuration would include, for example, a miniature pressure transducer (such as a Mikro-Tip® brand pressure transducer available from Millar Instruments, Inc., 6001 Gulf Freeway, Houston, Tex. 77023-5417) embedded or surrounded by a liquid, gas, or gel-filled balloon (at constant volume). As a counter-pressure balloon is slowly inflated, it would push the smaller catheter balloon into contact against the esophageal wall, causing gradually increasing pressure from the left atrium to be seen by the transducer. One advantage of this alternative embodiment is that it would likely be smaller than even the isovolumetric balloon embodiment.

It should be further understood that, although specific materials, shapes and dimensions are described herein (e.g., Exxon Extrel® SF brand polyethylene film, brand catheters, etc.) to illustrate a best mode example of the invention, the claims are in no way intended to be restricted to catheters and balloons constructed from these specific materials, or having specific shapes or dimensions. One having ordinary skill in the art can readily imagine a variety of materials for construction and a similar variety of geometries, shapes and dimensions for the various balloons and catheters described herein without departing from the spirit and scope of the appended claims.

METHOD FOR CORRECTING FOR POSITIVE END EXPIRATORY PRESSURE

The present invention is uniquely capable of providing correct measurement of mean left atrial pressure for patients connected to respirators. When a patient is connected to a breathing machine which uses positive end expiratory pressure (PEEP), the patient's pulmonary capillary wedge pressure (PCWP) and mean left atrial pressure (MLAP) may appear falsely elevated as a result, since all intra thoracic structures are exposed to varying degrees to this pressure. Since esophageal pressure ($P_E$) reflects intra pleural pressure (a good measure of the pressure environment in the chest), the effects of PEEP can be eliminated during measurement of mean left atrial pressure by first measuring the esophageal pressure using a nearly collapsed counter pressure balloon. Then an MLAP reading can be done in the usual manner. The corrected (for PEEP effect) mean left atrial pressure can then be calculated as follows:

$$MLAP_{corrected} = MLAP_{measured} - P_E$$

This correction can easily be achieved using the counter-pressure balloon with either the isovolumetric or flutter-valve embodiments.

EXPERIMENTAL TEST RESULTS

1. Laboratory Tests

As is customary in the medical device art, the present invention has been subjected to extensive laboratory testing by the inventor. Various mechanical devices were developed to simulate the heart-esophagus pressure environment. The first such device comprised rubber or polyethylene film bladders that were inserted into rigid cylinders and caused to pulsate at physiologic pressures and rates by a high frequency, adjustable stroke ventilator, capable of providing sinusoidally oscillating pressures at frequencies of up to 9 Hz. This approach was later abandoned in favor of a more sophisticated transparent "bell jar" pressure chamber in which various test catheters were placed. This chamber could be set at a given mean or background pressure, and the pressure could then be oscillated around the mean by the high frequency ventilator. Using this chamber, models of perfect, partial and imperfect balloon-atrial pressure coupling were tested. An additional pressure vessel was occasionally connected in parallel with the main test chamber to provide capacitance in the system.

Two versions of an inner test chamber were also constructed. A first version comprised a shallow cylinder that was closed at one end. An elastic diaphragm (usually rubber dental dam) was used to seal the other end. Test balloons were placed inside these chambers on pedestals of varying height (to regulate the initial distance between empty balloon and diaphragm). The pressure inside the inner chamber could be set to any level (usually 1 ATA) to simulate intra-esophageal pressures, while the pressure outside the inner chamber was set to the test pressure, causing the diaphragm to push downward in a concave fashion into the inner chamber. The diaphragm could then be set to oscillate by the high frequency ventilator, and thereby simulate the left atrium pressing on an esophageal balloon.

A second inner test chamber comprised a vertical cylinder with single openings on either side of the transverse (horizontal) axis, on center, through which a flexible latex tube passed, the tube being in communication with the pressure environment of the larger outer chamber. Vertical supports on either side of the transverse tube were provided for mounting test balloons, such that the balloons would come into contact with the transverse tube. The inner test chamber was typically vented to one atmosphere. During a test, the air pressure in the main chamber was set to oscillate by the high frequency ventilator, thereby causing the transverse latex tube to oscillate as well, thus simulating left atrial (or pulmonary venous) pulsations.

Adverting now to the drawings, FIGS. 10A-10G represent typical test results obtained with a first embodiment of the invention comprising a combination isovolumetric-counter pressure balloon-containing catheter, and FIGS. 11A-11E represent similar results obtained with a second embodiment comprising a flutter-valve catheter.

Figure 10A:
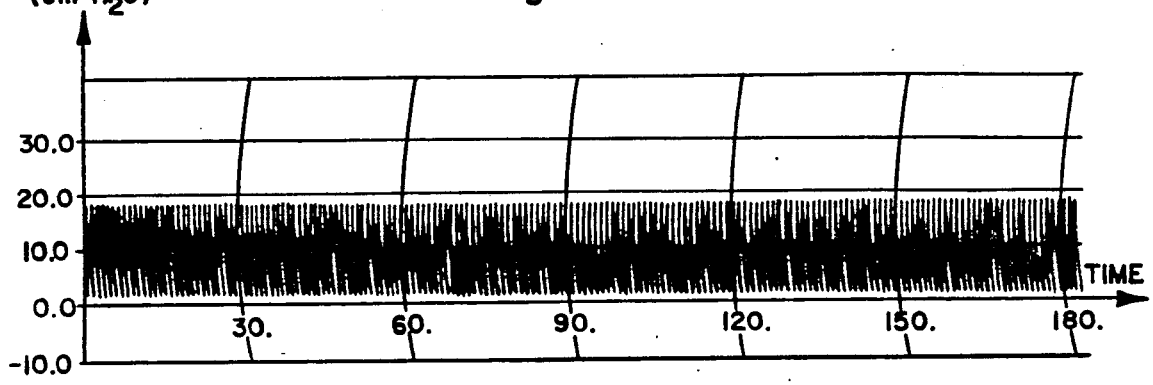
Figure 10B:
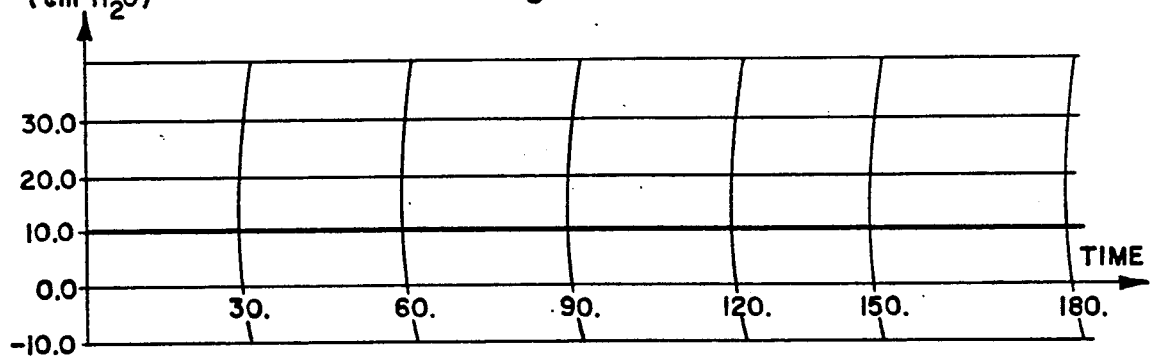

FIG. 10A shows the absolute heart simulator pressure similar to that which could be expected to be measured in a human subject. The absolute pressure is shown to oscillate between a range of 1-19 cm $H_2O$. FIG. 10B shows the mean heart simulator pressure derived from the absolute pressure of FIG. 10A. It is this pressure, representative of the mean left atrial pressure, which the present invention seeks to measure.

Figure 10C:
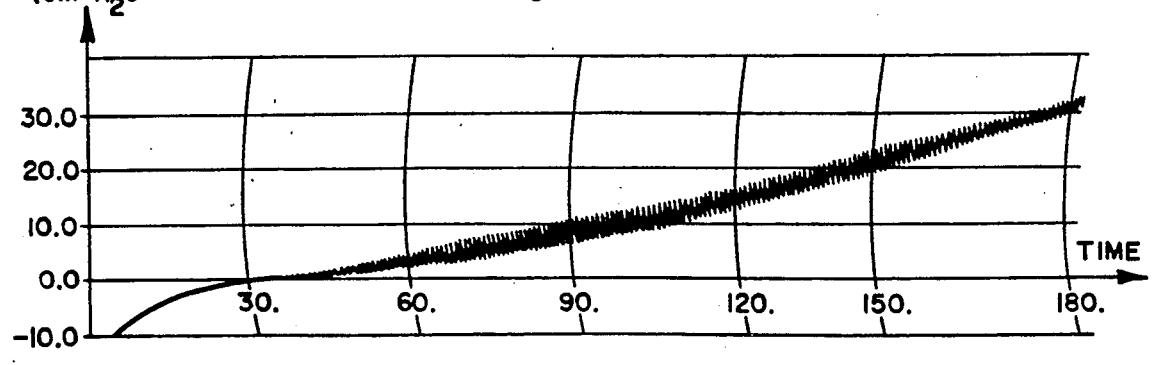

Adverting now to FIG. 10C, the absolute pressure in the isovolumetric balloon-containing catheter is shown as the balloon is slowly inflated. As mentioned previously, the isovolumetric balloon pressure is slowly regulated from a negative pressure (vacuum) to a positive pressure. As the pressure within the balloon becomes positive, the pressure begins to oscillate in response to the driving pressure of the heart.

The waveform of FIG. 10E is inverted and then added to the original signal (FIG. 10C) to obtain a steady baseline waveform as shown in FIG. 10D. The gain of the signal depicted in FIG. 10D has also been increased by a factor of about 6 over the original signal. The waveform of FIG. 10D is an oscillating signal of varying amplitude. The inventor has discovered that the point of maximum amplitude of the signal depicted in FIG. 10D corresponds to the point of concern, i.e., the mean left atrial pressure. For example, FIG. 10E represents the mean pressure of the waveform shown in FIG. 10C. The maximum amplitude of the signal of FIG. 10D occurs between times, t=80 to t=85. This enables one having ordinary skill in the art to read the mean left atrial pressure (MLAP) off FIG. 10E, which indicates an MLAP of approximately 7.0 cm $H_2O$, relatively close to the 10.0 cm $H_2O$ actual pressure as shown in FIG. 10B. This illustration represents one isolated reading. When a series of simulated mean left atrial pressures were studied at 5 cm $H_2O$ pressure increments from 0 cm $H_2O$ to 40 cm $H_2O$, the measured pressures were generally within 2 cm $H_2O$ of the actual pressures. Furthermore, linear regression of measured pressures against atrial pressures typically yielded an equation $y = -2.2 + 0.97x$ where x=measured pressure, y=actual pressure with a regression coefficient r=0.994. Of course, this relatively crude method of reading the pressures off strip charts can easily be automated. For example, an electronic peak detector could be used to sense the maximum amplitude of the isovolumetric pressure wave, and associated electronics could then determine and display the corresponding MLAP.

FIG. 10F represents the absolute pressure within the counter-pressure balloon. Again, the pressure rises uniformly from a negative pressure to a positive pressure. FIG. 10G represents the mean pressure within the counter-pressure balloon, which is derived from the waveform of FIG. 10F. A comparison of FIGS. 10E and 10G reveals that the mean pressures within the isovolumetric and counter-pressure balloons are nearly identical (for positive pressures) which ensures reliability of the test.

Figure 11A:
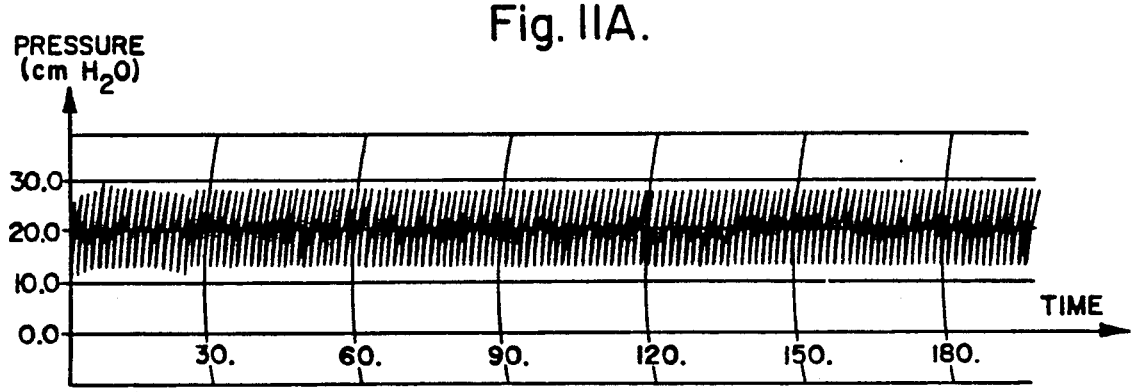
Figure 11B:
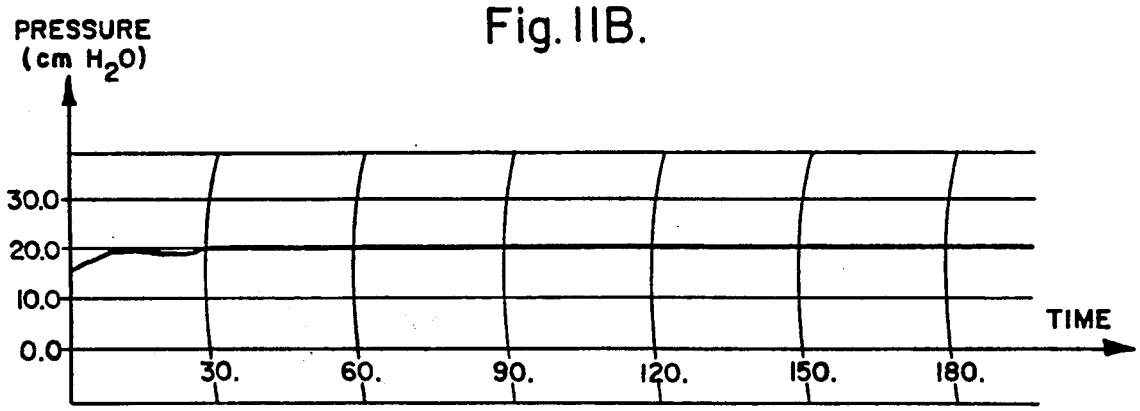
Figure 11C:
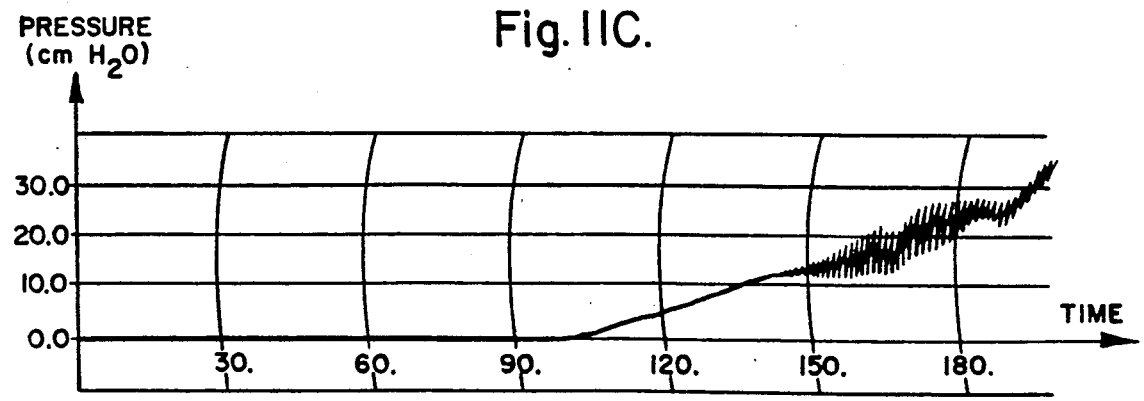

FIGS. 11A–11E represent a similar test for the flutter-valve embodiment. FIG. 11A represents the absolute pressure of the simulation heart and FIG. 11B is the mean pressure of the signal of FIG. 11A. As shown, the mean pressure sought to be measured is 20.0 cm $H_2O$. FIG. 11C represents the absolute pressure within the flutter-valve balloon. It should be noted that some minor experimentation may be required to obtain the oscillometric waveform shown in FIG. 11C. For example, minor adjustments of flow rate and back pressure may be necessary to achieve the proper waveform.

FIG. 11D is a steady baseline, increased gain (3×) representation of the signal of FIG. 11C, obtained by inverting the signal of FIG. 11E, adding the inverted signal to the original signal (FIG. 11C) and amplifying the result. Adverting to FIG. 11D, a peak or maximum is seen to occur at time t=169. This corresponds to a mean left atrial pressure of approximately 19.0 cm $H_2O$ as shown in FIG. 11E, which represents the mean pressure of the signal of FIG. 11D. Thus, it is seen that the flutter-valve method yields a measured pressure (19.0 cm $H_2O$) which is very close to the target heart simulation pressure (20.0 cm $H_2O$). The inventor has found that the flutter-valve method generally provides superior results to the isovolumetric/counter-pressure balloon method.

2. Human Tests

Upon completion of extensive bench testing of the present invention, the Institutional Review Board (IRB) at the University at Buffalo, State University of New York, unanimously approved the esophageal balloon-containing catheter as a "non-significant risk" device as defined by Food and Drug Administration regulation 21 C.F.R. 812.5(m) (1987), a preliminary requirement for obtainment of an Investigational Device Exemption for the catheter. The IRB found the device to be a non-significant risk for the following reasons:
1. It is a non-invasive technique since the gastro-intestinal tract is physiologically so constructed as to serve as a barrier to environmental foreign substances.
2. It is less hazardous than the clinically indicated Swan-Ganz catheter which is invasive in application.
3. The large experience of the investigators over several years with naso-gastric and esophageal intubations without incident (i.e., vagal-vagal reactions, reflux emesis and aspiration).
4. The limited expandability of the balloon coupled with maximal pressure of 50 mm Hg (where 300–620 mm Hg is used clinically and routinely) essentially provides practically no risk of esophageal rupture.

Subsequent to the IRB determination, the Human Research Committee at Millard Fillmore Hospitals, Buffalo, New York, granted approval for human testing of the present invention. At the time of filing the application for this patent, all necessary approvals to test the embodiments disclosed herein in healthy volunteers, or in actual patients who have indwelling Swan-Ganz catheters, have been obtained. However, at the time of filing, actual human testing of the embodiments disclosed herein has not occurred.

Human tests have been conducted, however, on an earlier embodiment of the present invention, comprising a two-balloon catheter having a lower atrial pressure sensing balloon (approximate volume of 4 mL) and an upper bias balloon (approximate volume of 2.3 mL). The bias balloon was used to eliminate respiratory pressure excursions in the esophagus. Both balloons were constructed of Exxon Extrel ® SF brand polyethylene film. The lower and upper balloons were connected in tandem and spaced longitudinally within the esophagus, and were not in contact with one another. The in vivo tests were conducted by and on the inventor himself to verify the theoretical principles upon which the present invention is based. These test results are represented in FIGS. 12A–12D.

Figure 12A:
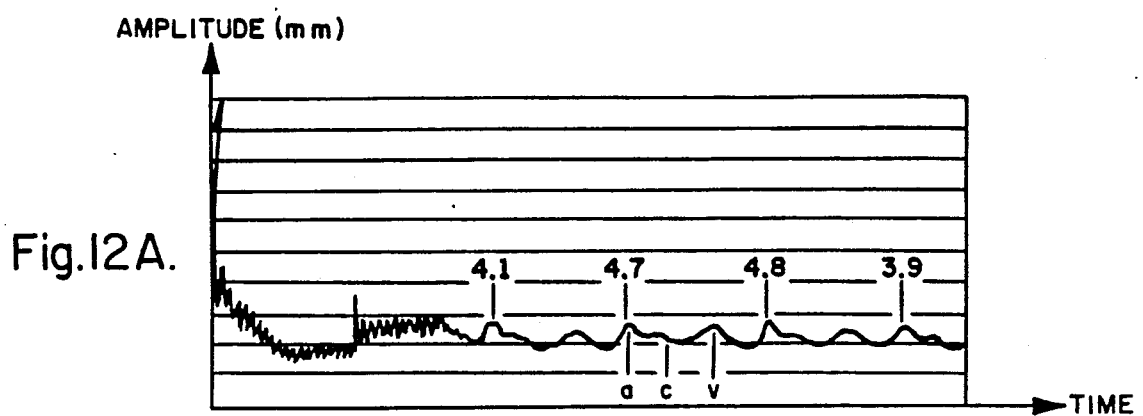
FIGS. 12A-12D depict left atrial pressure traces from a 4 mL esophageal balloon in an upright subject.
Figure 12B:
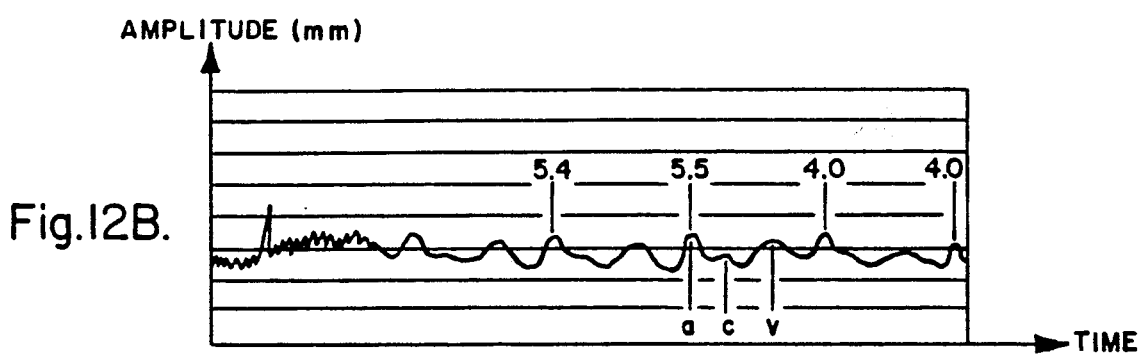
Figure 12C:
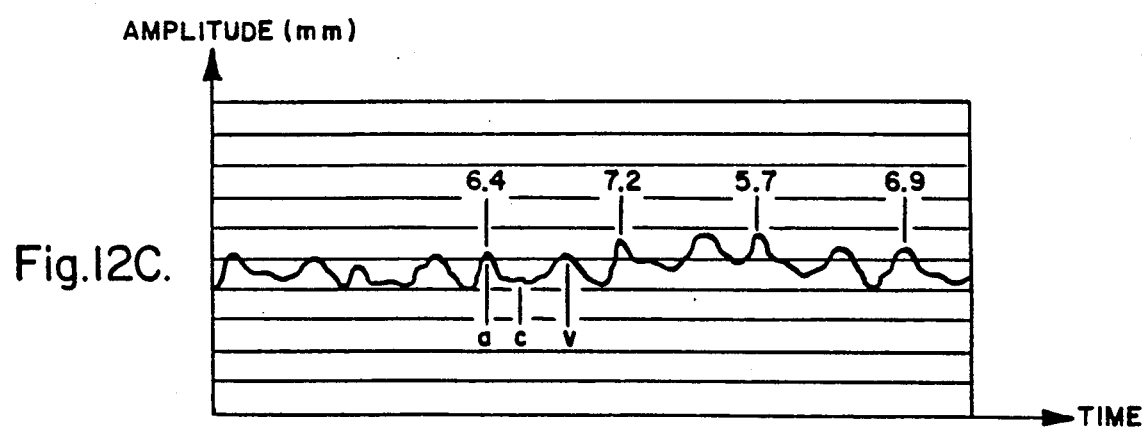
Figure 12D:
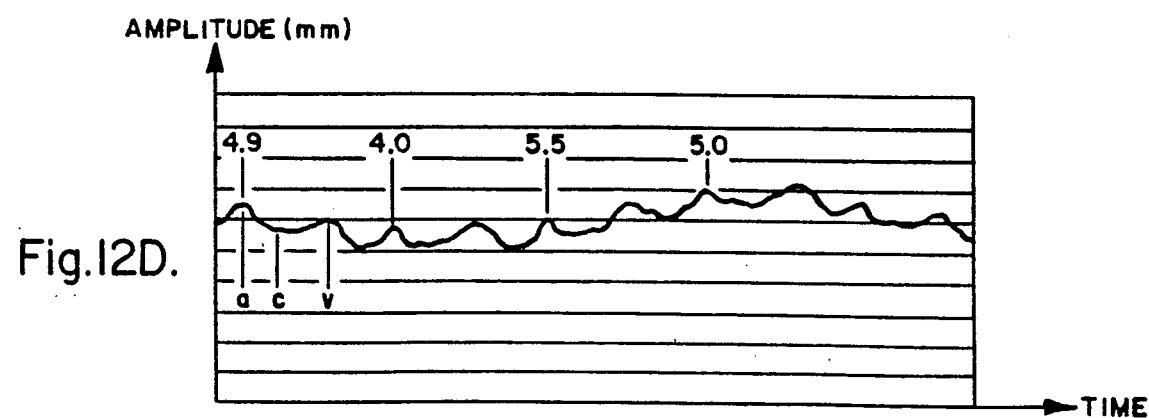

Adverting now to FIGS. 12A–12D, left atrial pressure traces from a 4 mL esophageal balloon in an upright subject are depicted. The "a", "c" and "v" waves are marked and timing was confirmed by simultaneous electrocardiogram. The "a", "c" and "v" waves are three essential components of the left atrial pressure wave. The time scale (x axis) for FIGS. 12A–12D is greatly expanded relative to FIGS. 10 and 11. FIG. 12A illustrates the trace obtained with a balloon volume of 1 mL, resulting in a mean amplitude of "a" wave equal to 4.4 mm, and a mean balloon pressure of 1 cm $H_2O$. FIG. 12B illustrates the trace obtained with a balloon volume of 2 mL, resulting in a mean amplitude of "a" wave equal to 4.7 mm, and a mean balloon pressure of 4 cm $H_2O$. FIG. 12C illustrates the trace obtained with a balloon volume of 3 mL, resulting in a mean amplitude of "a" wave equal to 6.6 mm, and a mean balloon pressure of 12 cm $H_2O$. FIG. 12D illustrates the trace obtained with a balloon volume of 3.5 mL, resulting in a mean amplitude of "a" wave equal to 4.9 mm, and a mean balloon pressure of 18 cm $H_2O$. FIGS. 12A–12D show that the oscillometric effect appeared to be operative, with peak amplitude seen at a mean balloon pressure of 12 cm $H_2O$ (FIG. 12C). Assuming that the mean pressure of the balloon equals the mean left atrial pressure at the point of peak amplitude, then FIG. 12C indicates a mean left atrial pressure of 9 mm Hg. This is well within the expected range of physiological pressures.

It will be understood that the foregoing description is illustrative of the invention and should not be considered as limiting and that other embodiments of the invention are possible without departing from the invention's spirit and scope.

What is claimed is:
1. A method for measuring left atrial pressure, comprising:
    inserting a balloon-containing catheter into the esophagus and positioning said catheter so that when the balloon is inflated, pressure from the left atrium affects said balloon;
    inflating said balloon; and determining mean left atrial pressure by the effect of the atrial pressure upon said balloon.

2. A method as recited in claim 1 wherein said positioning comprises:
inserting a positioning balloon through the pharynx, down the esophagus, and into the stomach, wherein said positioning balloon is connected to a tethering catheter which extends upwardly from the stomach and exits the nose, wherein said balloon-containing catheter is tied to said tethering catheter at a predetermined distance from the positioning balloon, said predetermined distance corresponding approximately to the relatively constant distance in man between the esophago-gastric junction and the left atrium;
inflating said positioning balloon to a sufficient size such that it will not pass through the esophago-gastric junction; and
applying gentle traction at the nose to said tethering catheter to keep said balloon-containing catheter in position in the esophagus proximate the left atrium.

3. A method as recited in claim 1 wherein said balloon-containing catheter comprises a first catheter and a counter-pressure balloon connected to said first catheter and a second catheter and an isovolumetric balloon connected to said second catheter and said positioning further comprises arranging said counter-pressure balloon and said isovolumetric balloon to be in substantial contact with one another and said determining further comprises determining the effect of atrial pressure upon both said counter-pressure and isovolumetric balloons.

4. A method as recited in claim 3 wherein said inflating comprises regulating compressed gas in said first and second catheters and maintaining approximately equal pressures in said balloons.

5. A method as recited in claim 4 wherein the pressure of the gas in said first and second catheters is gradually increased to a maximum pressure of approximately 50 cm $H_2O$.

6. A method as recited in claim 4 wherein said determining comprises converting measured pressures in said catheters to electrical signals by means of pressure transducers and displaying said signals as representative of left atrial pressure.

7. A method as recited in claim 1 wherein said balloon-containing catheter comprises a first catheter and a counter-pressure connected to said first catheter and a second catheter and a flutter-valve balloon connected to said second catheter and said positioning further comprises arranging said counter-pressure balloon and said flutter-valve balloon to be in substantial contact with one another and said determining further comprises determining the effect of atrial pressure upon said flutter-valve balloon.

8. A method as recited in claim 7 wherein said inflating comprises gradually and uniformly increasing the flow rate of gas into said first and second catheters from a low rate of approximately 0.2 mL/min. to a maximum flow rate of approximately 4.0 mL/min.

9. A method for measuring left atrial pressure, comprising:
inserting a sensing probe into the esophagus; and,
positioning said probe so that absolute pressure from the left atrium is determined by said probe.

10. A method for correcting mean left atrial pressure measurements for a person connected to a breathing machine for the effect of positive end expiratory pressure, comprising:

measuring esophageal pressure using a nearly collapsed balloon while a person is connected to said breathing machine;
measuring mean left atrial pressure by inserting a sensing probe into the esophagus and positioning said probe so that pressure from the left atrium is sensed by said probe; and,
calculating corrected mean left atrial pressure from the equation:

$$MLAP_{corrected} = MLAP_{measured} - P_E$$

where,
$MLAP_{corrected}$ is the corrected mean left atrial pressure;
$MLAP_{measured}$ is the measured mean left atrial pressure; and,
$P_E$ is the measured esophageal pressure.

11. Apparatus for measuring left atrial pressure, comprising:
a balloon-containing catheter adapted to be insertable into an esophagus;
means for positioning said balloon-containing catheter in the esophagus such that when the balloon is inflated, pressure from the left atrium affects said balloon;
means for inflating said balloon; and
means for determining mean left atrial pressure by the effect of the atrial pressure upon said balloon.

12. Apparatus as recited in claim 11 wherein said means for positioning comprises:
a positioning balloon adapted to be insertable through the nose, down the esophagus and into the stomach; and
a tethering catheter attached to said positioning balloon at a distal end of said catheter and adapted to be insertable into the nose, down the esophagus and into the stomach,-said tethering catheter tied to said balloon-containing catheter so the balloon of the balloon-containing catheter is at a predetermined distance from said positioning balloon, said distance corresponding approximately to the relatively constant distance in man between the esophago-gastric junction and the left atrium,
wherein said tethering catheter positions the balloon of said balloon-containing catheter proximate the left atrium when said positioning balloon is inflated in the stomach and gentle traction is applied to said tethering catheter at the nose so as to raise said positioning balloon to the esophago-gastric junction.

13. Apparatus as recited in claim 11 wherein said balloon-containing catheter comprises:
a counter-pressure balloon connected to a first catheter; and
an isovolumetric balloon connected to a second catheter,
wherein said counter-pressure balloon and said isovolumetric balloon are arranged to be in substantial contact with one another, and wherein left atrial pressure is determined by the effect of atrial pressure upon both said counter-pressure and isovolumetric balloons.

14. Apparatus as recited in claim 13 wherein said means for inflating comprises:
a source of compressed gas; and
means for regulating the flow and pressure of said gas in each of said first and second catheters and for maintaining approximately equal pressures in said counter-pressure and isovolumetric balloons.

15. Apparatus as recited in claim 11 wherein said balloon-containing catheter comprises:
   a first catheter;
   a counter-pressure balloon connected to said first catheter;
   a second catheter; and
   an isovolumetric balloon connected to said second catheter;
   wherein said counter-pressure balloon and said isovolumetric balloon are arranged to be in substantial contact with one another, and wherein left atrial pressure is determined by the effect of atrial pressure upon both said counter-pressure and isovolumetric balloons.

16. An esophageal balloon-containing catheter for sensing and measuring left atrial pressure, comprising:
   a first catheter,
   a counter-pressure balloon connected to said first catheter;
   a second catheter having an inlet section and an exhaust section; and
   a flutter-valve balloon connected to said second catheter,
   wherein said counter-pressure balloon and said flutter-valve balloon are arranged to be in substantial contact with one another, and wherein mean left atrial pressure is determined by the effect of atrial pressure upon said flutter-valve balloons.

17. Apparatus as recited in claim 16 wherein said flutter-valve balloon comprises a balloon membrane formed of low density polyethylene film which is secured to said second catheter between said inlet and exhaust sections.

18. Apparatus as recited in claim 16 wherein said polyethylene film has a thickness of 0.0005 inches.

19. Apparatus as recited in claim 18 wherein said balloon has a length of approximately 35 millimeters between said inlet and exhaust sections and a width of approximately 4 millimeters.

20. Apparatus for measuring left atrial pressure, comprising:
   means for inserting a sensing probe into the esophagus; and
   means for positioning said probe so that mean pressure from the left atrium is determined by said probe.

21. Apparatus as recited in claim 20 wherein said sensing probe comprises a catheter-mounted miniature pressure transducer.

22. Apparatus for correcting mean left atrial pressure measurements while a person is connected to a breathing machine for the effect of positive end expiratory pressure, comprising:
   means for measuring esophageal pressure using a nearly collapsed balloon while a person is connected to said breathing machine;
   means for measuring mean left atrial pressure by inserting a sensing probe into the esophagus and positioning said probe so that pressure from the left atrium is sensed by said probe; and
   means for calculating corrected mean left atrial pressure from the equation:

$$MLAP_{corrected} = MLAP_{measured} - P_E$$

where,
$MLAP_{corrected}$ is the corrected mean left atrial pressure;
$MLAP_{measured}$ is the measured mean left atrial pressure; and,
$P_E$ is the measured esophageal pressure.

23. Apparatus as recited in claim 20 wherein said sensing probe comprises a balloon.

* * * * *